US010738352B2

(12) United States Patent
Hashimoto et al.

(10) Patent No.: US 10,738,352 B2
(45) Date of Patent: Aug. 11, 2020

(54) METHOD FOR ANALYZING NUCLEIC ACID DERIVED FROM SINGLE CELL

(71) Applicant: IDAC THERANOSTICS, INC., Tokyo (JP)

(72) Inventors: Shin-ichi Hashimoto, Ishikawa (JP); Shuichi Kaneko, Ishikawa (JP); Kouji Matsushima, Tokyo (JP)

(73) Assignee: IDAC THERANOSTICS, INC., Tokyo (JP)

( * ) Notice: Subject to any disclaimer, the term of this patent is extended or adjusted under 35 U.S.C. 154(b) by 728 days.

(21) Appl. No.: 15/308,110

(22) PCT Filed: Apr. 7, 2015

(86) PCT No.: PCT/JP2015/060841
§ 371 (c)(1),
(2) Date: Nov. 1, 2016

(87) PCT Pub. No.: WO2015/166768
PCT Pub. Date: Nov. 5, 2015

(65) Prior Publication Data
US 2017/0166959 A1    Jun. 15, 2017

(30) Foreign Application Priority Data

May 2, 2014   (JP) .................................. 2014-095011

(51) Int. Cl.
| | |
|---|---|
| *C12Q 1/6837* | (2018.01) |
| *C12Q 1/6844* | (2018.01) |
| *C12N 15/10* | (2006.01) |
| *C12Q 1/6806* | (2018.01) |
| *C12Q 1/6874* | (2018.01) |
| *C40B 20/04* | (2006.01) |
| *C40B 40/06* | (2006.01) |
| *C12N 15/09* | (2006.01) |

(52) U.S. Cl.
CPC ........... *C12Q 1/6837* (2013.01); *C12N 15/09* (2013.01); *C12N 15/1006* (2013.01); *C12Q 1/6806* (2013.01); *C12Q 1/6844* (2013.01); *C12Q 1/6874* (2013.01); *C40B 20/04* (2013.01); *C40B 40/06* (2013.01)

(58) Field of Classification Search
None
See application file for complete search history.

(56) References Cited

U.S. PATENT DOCUMENTS

| | | | |
|---|---|---|---|
| 6,309,824 B1 | 10/2001 | Drmanac | |
| 2003/0082584 A1 | 5/2003 | Shi et al. | |
| 2004/0219516 A1 | 11/2004 | Bennett et al. | |
| 2005/0100900 A1 | 5/2005 | Kawashima et al. | |
| 2013/0203605 A1 | 8/2013 | Shendure et al. | |
| 2013/0274117 A1 | 10/2013 | Church et al. | |
| 2015/0299784 A1* | 10/2015 | Fan | C12Q 1/6874 506/4 |
| 2016/0244742 A1* | 8/2016 | Linnarsson | C12N 15/1065 |

FOREIGN PATENT DOCUMENTS

| | | |
|---|---|---|
| JP | 2010-110262 A | 5/2010 |
| WO | 2010-087466 A1 | 8/2010 |

OTHER PUBLICATIONS

Ahern (1995) "Biochemical, Reagents Kits Offer Scientists Good Return on Investment" The Scientist 9(15):20 (Year: 1995).*
International Search Report issued in corresponding International Patent Application No. PCT/JP2015/060841 dated Jul. 7, 2015 (2 pages).
Macaulay et al., "Single Cell Genomics: Advances and Future Perspectives," PLoS Genetics, 2014, vol. 10, No. 1, e1004126, pp. 1-9.
Margulies et al., "Genome sequencing in microfabricated high-density picolitre reactors," Nature, 2005, vol. 437, pp. 376-380.
Tang et al., "Development and applications of single-cell transcriptome analysis," Nature Methods Supplement, 2011, vol. 8, No. 4S, pp. S6-S11.
Xu et al., "Dual primer emulsion PCR for next-generation DNA sequencing," Biotechniques, 2010, vol. 48, No. 5, pp. 409-412 (pp. 1-6).

* cited by examiner

*Primary Examiner* — Kaijiang Zhang
(74) *Attorney, Agent, or Firm* — Kilyk & Bowersox, P.L.L.C.

(57) ABSTRACT

The present invention relates to a method of analyzing a composition of nucleic acids derived from a single cell using a microplate including a plurality of reaction wells, the microplate having one bead arranged in one reaction well, the one bead having bound thereto a plurality of molecules of single-stranded oligonucleotides, the single-stranded oligonucleotides each having a nucleic acid capture sequence exposed at the 3' end and a barcode sequence on the 5' side of the nucleic acid capture sequence, the barcode sequence including a base sequence that differs from bead to bead.

13 Claims, 9 Drawing Sheets
Specification includes a Sequence Listing.

[Figure 1A]
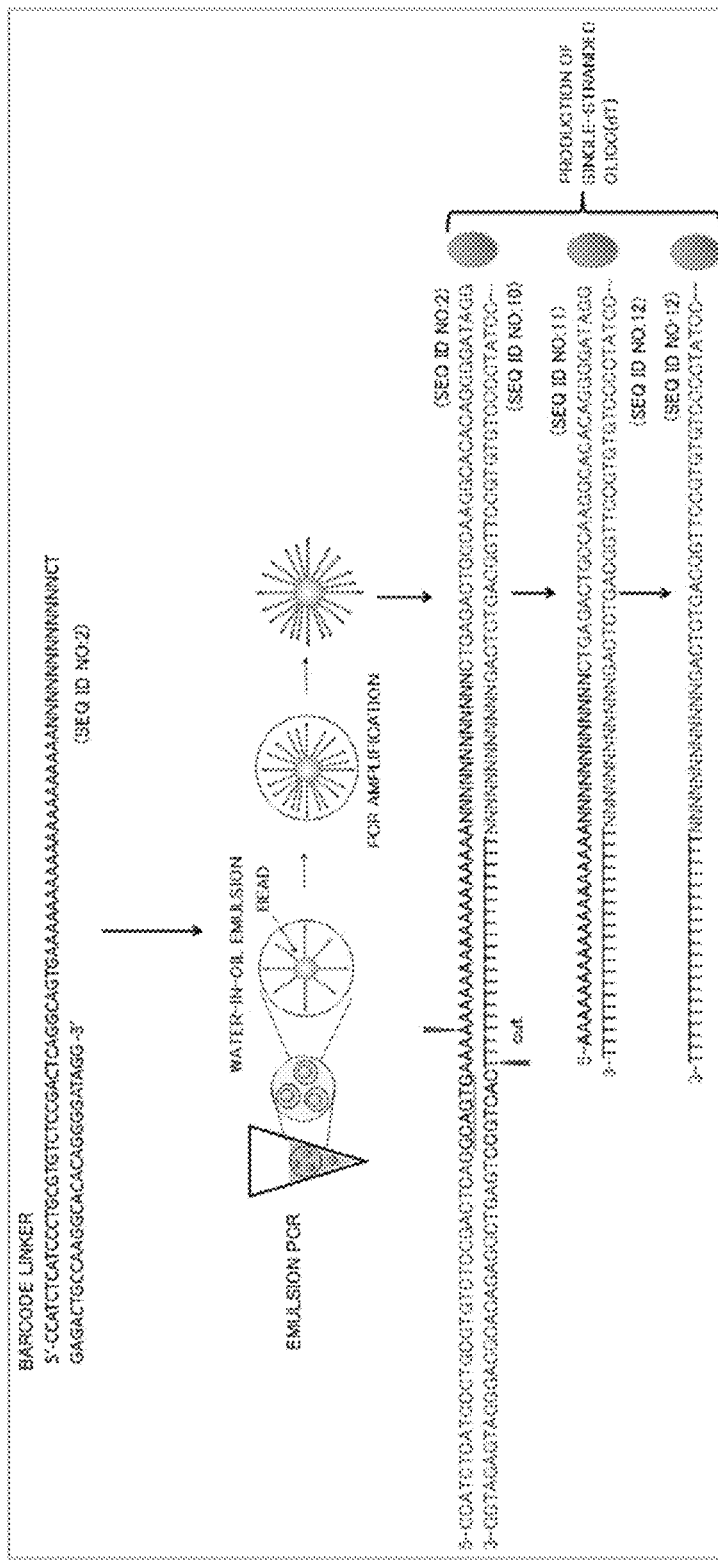

[Figure 1B]
[Figure 2]
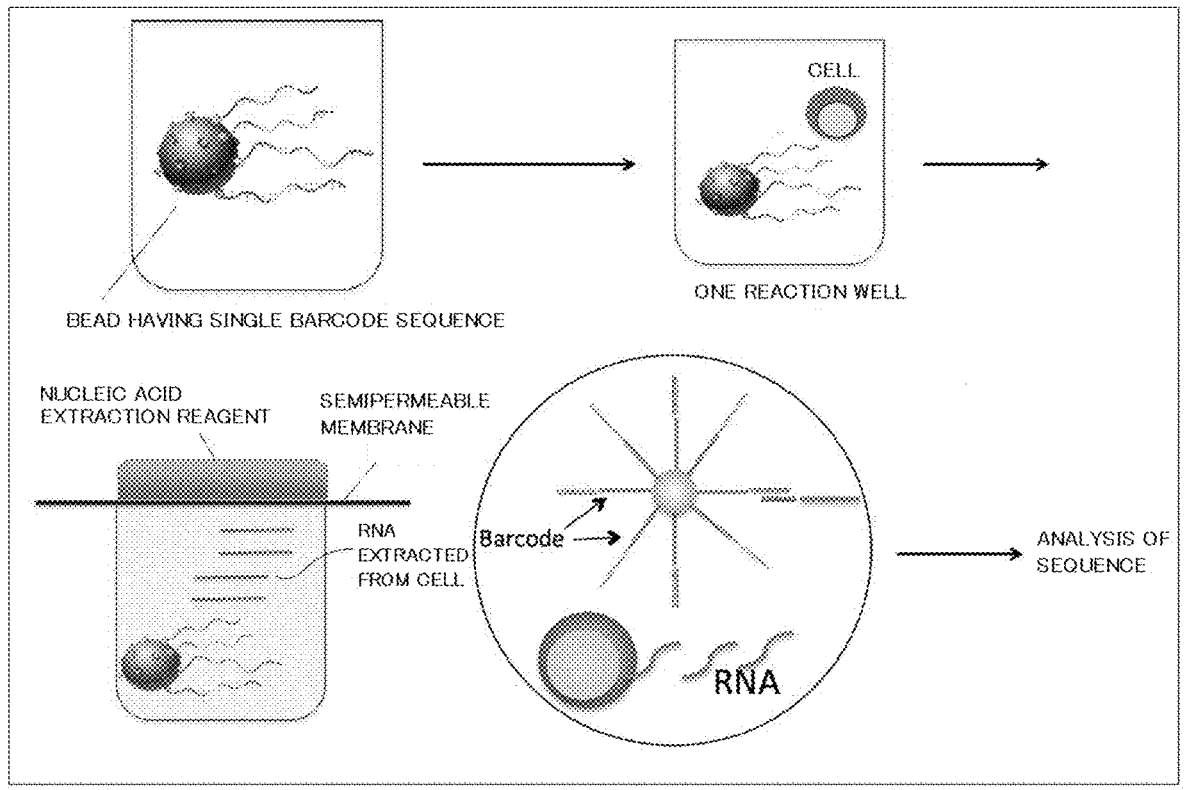

[Figure 3]

```
AATGATACGGCGACCACCGAGATCTACACTCTTTC
CCTACACGACGCTCTTCCGATCTCCTATCCCCTGTG
TGCCTTGGCAGTCTCAGCTATTCATTCTGTTTTTTTT
TTTTTTTTTTTTACTTTATTAAAATACTGAGTTTTATT
TCACATGTATATTTTGTCTCCCCACCACTTCCATGT
CTGACCACCGCTACTACTATGTCCTATCATAACATT
CCAAGATCGGAAGAGCACACGTCTGAACTCCAGTC
ACATCACGATCTCGTATGCCGTCTTCTGCTTG
                              (SEQ ID NO:30)
```

LINKER  BARCODE SEQUENCE  3' END OF mRNA DERIVED FROM CELL

[Figure 4]

Identification of genes from single cell by barcode

| Description | Barcode | | Description | Barcode | |
|---|---|---|---|---|---|
| RPL29 | AACGTGCTTGAA | (SEQ ID NO:35) | AAMDC | GNNGTTGCGGGT | (SEQ ID NO:63) |
| COX4I1 | ACATTGGTCTTG | (SEQ ID NO:36) | C9orf16 | TGTGTCTTAACC | (SEQ ID NO:64) |
| FAM192A | AGTTCCCCGACC | (SEQ ID NO:37) | COX4I1 | ACATTGGTCTTG | (SEQ ID NO:65) |
| RPL32 | CAGAGGAACTAG | (SEQ ID NO:38) | COX4I1 | TTCTTTACCAAT | (SEQ ID NO:66) |
| FUOM | CCATGGTTTAGG | (SEQ ID NO:39) | EIF4A1 | TCGCACGCGGTA | (SEQ ID NO:67) |
| MZT2B | CGTCAATCTTTT | (SEQ ID NO:40) | ENO1 | TTCGAACAGTAA | (SEQ ID NO:68) |
| FTL | CTTTATATTTTT | (SEQ ID NO:41) | FAM192A | AGTTCCCCGACC | (SEQ ID NO:69) |
| VPS9D1 | GAAGATCAGAGT | (SEQ ID NO:42) | FDFT1 | GTGTTCGTCTTC | (SEQ ID NO:70) |
| RPS18 | GCAGCTTGGGGT | (SEQ ID NO:43) | FTL | CTTTATATTTTT | (SEQ ID NO:71) |
| AAMDC | GNNGTTGCGGGT | (SEQ ID NO:44) | FUOM | CCATGGTTTAGG | (SEQ ID NO:72) |
| RPS14 | GTACCCTATATC | (SEQ ID NO:45) | GPX4 | GTGCTAGTGGGG | (SEQ ID NO:73) |
| GPX4 | GTGCTAGTGGGG | (SEQ ID NO:46) | MIF | TTATAGTTCGTG | (SEQ ID NO:74) |
| RPS15 | GTGCTAGTGNNT | (SEQ ID NO:47) | MIF | TTGTTGTCCGTT | (SEQ ID NO:75) |
| FDFT1 | GTGTTCGTCTTC | (SEQ ID NO:48) | MZT2B | CGTCAATCTTTT | (SEQ ID NO:76) |
| NDUFB7 | TAGTTTCTGTAG | (SEQ ID NO:49) | NDUFB7 | TAGTTTCTGTAG | (SEQ ID NO:77) |
| RPS16 | TATGGAGTTTTG | (SEQ ID NO:50) | RPL10 | TGAACCACGCGC | (SEQ ID NO:78) |
| RPLP1 | TCGAAGTNNNAT | (SEQ ID NO:51) | RPL28 | TTGTTAGGTTAC | (SEQ ID NO:79) |
| EIF4A1 | TCGCACGCGGTA | (SEQ ID NO:52) | RPL29 | AACGTGCTTGAA | (SEQ ID NO:80) |
| RPL10 | TGAACCACGCGC | (SEQ ID NO:53) | RPL32 | CAGAGGAACTAG | (SEQ ID NO:81) |
| C9orf16 | TGTGTCTTAACC | (SEQ ID NO:54) | RPLP1 | TCGAAGTNNNAT | (SEQ ID NO:82) |
| MIF | TTATAGTTCGTG | (SEQ ID NO:55) | RPS14 | GTACCCTATATC | (SEQ ID NO:83) |
| TPI1 | TTCCTCGGCTAT | (SEQ ID NO:56) | RPS15 | GTGCTAGTGNNT | (SEQ ID NO:84) |
| ENO1 | TTCGAACAGTAA | (SEQ ID NO:57) | RPS18 | GCAGCTTGGGGT | (SEQ ID NO:85) |
| COX4I1 | TTCTTTACCAAT | (SEQ ID NO:58) | RPS16 | TATGGAGTTTTG | (SEQ ID NO:86) |
| TRAPPC5 | TTCTTTACCAAT | (SEQ ID NO:59) | RPS16 | TTTGGAGTCAGA | (SEQ ID NO:87) |
| RPL28 | TTGTTAGGTTAC | (SEQ ID NO:60) | TM7SF2 | TTTGAAAGCTGT | (SEQ ID NO:88) |
| MIF | TTGTTGTCCGTT | (SEQ ID NO:61) | TPI1 | TTCCTCGGCTAT | (SEQ ID NO:89) |
| TM7SF2 | TTTGAAAGCTGT | (SEQ ID NO:62) | TRAPPC5 | TTCTTTACCAAT | (SEQ ID NO:90) |
| RPS16 | TTTGGAGTCAGA | (SEQ ID NO:62) | VPS9D1 | GAAGATCAGAGT | (SEQ ID NO:91) |

[Figure 5]

RELATIONSHIP BETWEEN NUMBER OF SEQUENCES AND GENES

| Barcode | | | NUMBER OF GENES | NUMBER OF READS SEQUENCED |
|---|---|---|---|---|
| CELL 1 | AGGTCAAAGGAT | (SEQ ID NO:92) | 12,045 | 6,651,413 |
| CELL 2 | TCTCATAATGTT | (SEQ ID NO:93) | 13,243 | 6,288,548 |
| CELL 3 | GTAGCGCGCTTT | (SEQ ID NO:94) | 12,316 | 6,248,299 |
| CELL 4 | AATTCTGATGCT | (SEQ ID NO:95) | 12,493 | 6,213,589 |
| CELL 5 | TTTTGTTGTATC | (SEQ ID NO:96) | 12,394 | 5,991,697 |
| CELL 6 | GCTATCGATTAT | (SEQ ID NO:97) | 12,391 | 5,451,596 |
| CELL 7 | TTTACCTGAGGG | (SEQ ID NO:98) | 11,600 | 5,003,586 |
| CELL 8 | TTACCCGTTTGG | (SEQ ID NO:99) | 11,208 | 4,973,078 |
| CELL 9 | TTCATTCTCTCT | (SEQ ID NO:100) | 11,862 | 4,627,022 |
| CELL 10 | GTCTCAGGTTCC | (SEQ ID NO:101) | 11,421 | 4,320,056 |
| CELL 11 | TACTGTTAATTT | (SEQ ID NO:102) | 11,418 | 4,267,290 |
| CELL 12 | TCTTCTGATTAA | (SEQ ID NO:103) | 11,868 | 4,239,379 |
| CELL 13 | GTTTTCTTCGAT | (SEQ ID NO:104) | 11,581 | 4,139,372 |
| CELL 14 | TGGCTTCAGATA | (SEQ ID NO:105) | 11,340 | 4,101,328 |
| CELL 15 | TGTTTTTTTAAG | (SEQ ID NO:106) | 11,407 | 3,943,317 |
| CELL 16 | AATGGAAGGCTA | (SEQ ID NO:107) | 10,035 | 3,759,568 |
| CELL 17 | CTTGCTCTATTG | (SEQ ID NO:108) | 11,404 | 3,543,093 |
| CELL 18 | ACGATTGATCTT | (SEQ ID NO:109) | 11,081 | 3,516,829 |
| CELL 19 | AGAATAGGAATA | (SEQ ID NO:110) | 11,284 | 3,480,795 |
| CELL 20 | CTGTACTGCGTA | (SEQ ID NO:111) | 10,130 | 3,411,037 |

[Figure 6]

GENES EXPRESSED IN RESPECTIVE CELLS (VALUES REPRESENT NUMBERS OF READS COUNTED)

| NAME OF GENE | BARCODE SEQUENCE | AGGTGAAGGAT (SEQ ID NO.92) CELL 1 | TGTCATAATGTT (SEQ ID NO.93) CELL 2 | GTAGCGCGGCTTT (SEQ ID NO.94) CELL 3 | AATTCTGATGGT (SEQ ID NO.95) CELL 4 | TTTGTTGTATC (SEQ ID NO.96) CELL 5 | GCTATCGATTAT (SEQ ID NO.97) CELL 6 | TTTACCTGAGGG (SEQ ID NO.98) CELL 7 |
|---|---|---|---|---|---|---|---|---|
| FTL | | 342,130 | 260,943 | 279,166 | 136,969 | 669,720 | 701,122 | 607,990 |
| FTH1 | | 177,283 | 62,047 | 94,250 | 67,488 | 314,338 | 120,431 | 217,562 |
| GAPDH | | 78,323 | 68,492 | 74,621 | 60,770 | 52,337 | 49,648 | 44,581 |
| KRT18 | | 59,882 | 57,534 | 23,111 | 37,680 | 24,410 | 46,594 | 15,840 |
| PFN1 | | 58,872 | 65,415 | 73,329 | 66,961 | 42,772 | 45,175 | 42,121 |
| TPI1 | | 58,711 | 39,907 | 39,936 | 43,093 | 25,820 | 31,114 | 21,842 |
| TMSB4X | | 52,250 | 16,880 | 27,929 | 30,727 | 25,953 | 10,967 | 20,404 |
| ANXA2 | | 47,819 | 56,870 | 55,495 | 86,776 | 27,093 | 52,619 | 44,047 |
| RPS2 | | 45,405 | 40,886 | 53,464 | 39,358 | 38,484 | 23,084 | 23,841 |
| ACTB | | 45,080 | 33,536 | 51,110 | 32,225 | 28,086 | 17,226 | 31,218 |
| KRT8 | | 42,964 | 37,698 | 12,553 | 36,511 | 17,062 | 20,038 | 13,866 |
| TNFRSF12A | | 41,869 | 29,737 | 28,346 | 29,473 | 17,662 | 22,046 | 18,946 |
| ACTG1 | | 39,891 | 41,751 | 42,604 | 30,460 | 25,290 | 17,757 | 29,756 |
| SH3BGRL3 | | 38,316 | 21,054 | 27,238 | 24,524 | 18,605 | 11,157 | 13,906 |
| MYL6 | | 37,588 | 14,624 | 24,020 | 21,829 | 13,980 | 15,392 | 16,490 |
| PPIA | | 35,596 | 21,867 | 29,753 | 24,400 | 18,046 | 16,850 | 15,831 |
| RPLP0 | | 33,577 | 20,797 | 26,307 | 24,759 | 19,981 | 14,397 | 18,482 |
| ENO1 | | 32,630 | 21,613 | 24,400 | 27,279 | 21,888 | 15,225 | 15,769 |
| RPS7 | | 30,011 | 30,214 | 34,266 | 28,702 | 31,029 | 20,234 | 26,183 |
| RPL10 | | 29,753 | 19,085 | 23,673 | 13,265 | 24,021 | 10,957 | 10,619 |
| TUBB | | 29,198 | 42,458 | 50,167 | 41,605 | 17,076 | 23,317 | 16,692 |
| ALDOA | | 27,052 | 15,654 | 16,859 | 17,754 | 13,102 | 18,963 | 14,745 |
| CD63 | | 26,369 | 19,017 | 18,024 | 18,985 | 27,414 | 12,387 | 15,260 |
| RPS5 | | 26,336 | 19,807 | 25,719 | 21,322 | 20,287 | 13,295 | 18,521 |
| HSPB1 | | 26,072 | 11,302 | 9,335 | 14,951 | 15,264 | 8,059 | 8,052 |
| OAZ1 | | 25,140 | 13,509 | 11,628 | 14,680 | 8,514 | 11,870 | 7,762 |
| CFL1 | | 24,934 | 12,283 | 18,902 | 13,206 | 10,676 | 13,343 | 7,064 |
| LCN2 | | 23,611 | 5,502 | 1,229 | 1,795 | 2,751 | 5,927 | 3,509 |
| PKM | | 23,108 | 18,660 | 25,255 | 29,843 | 15,560 | 17,604 | 21,726 |
| PHLDA2 | | 23,011 | 13,276 | 14,720 | 13,602 | 15,290 | 6,598 | 10,022 |

[Figure 7]
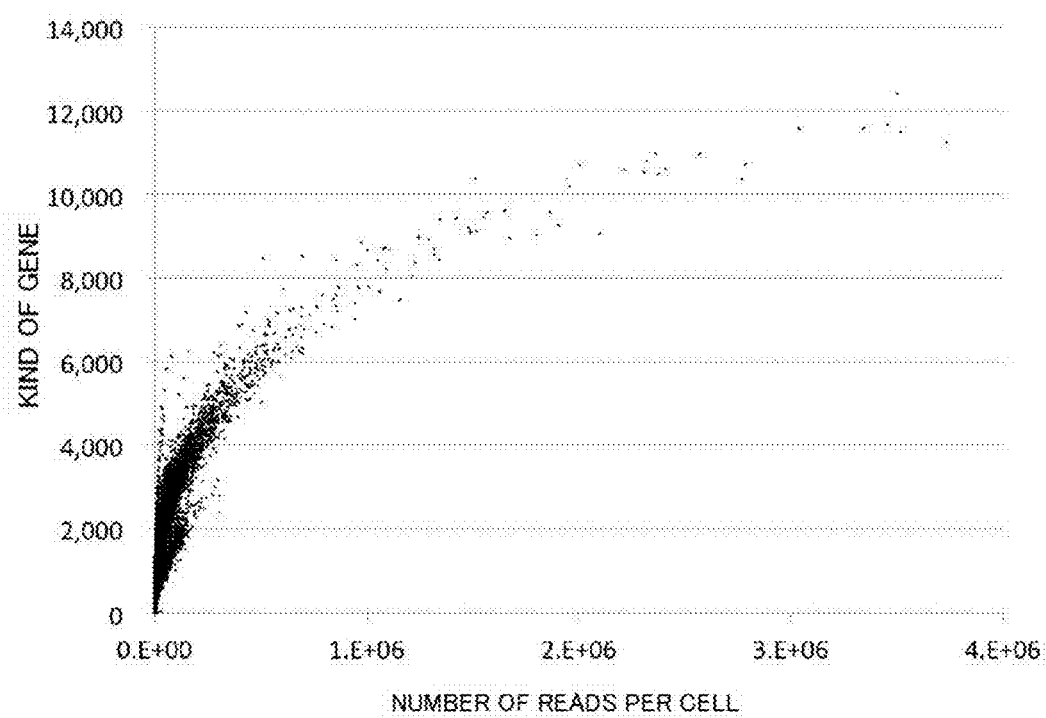

[Figure 8]
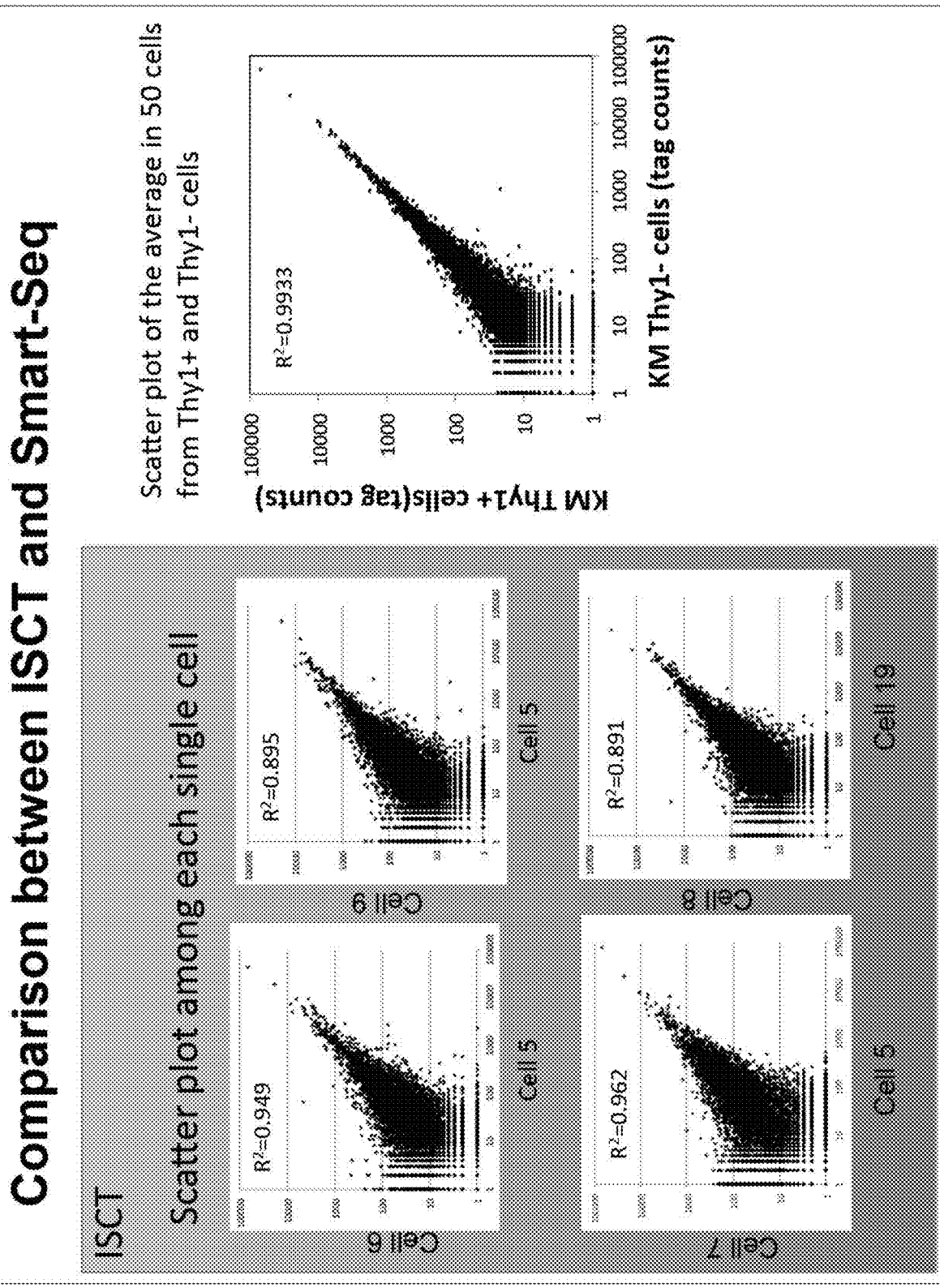

[Figure 9]
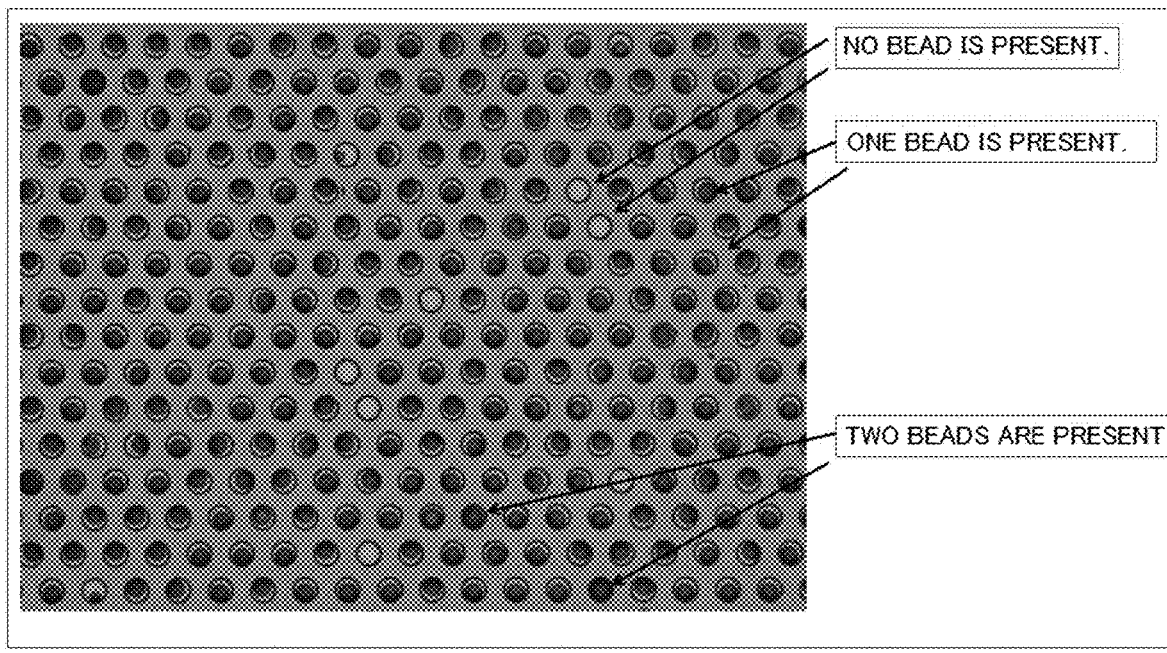

SEQUENCE LISTING

<160> NUMBER OF SEQ ID NOS: 111

<210> SEQ ID NO 1
<211> LENGTH: 12
<212> TYPE: DNA
<213> ORGANISM: Artificial Sequence
<220> FEATURE:
<223> OTHER INFORMATION: Barcode sequence
<220> FEATURE:
<221> NAME/KEY: misc_feature
<222> LOCATION: (1)..(12)
<223> OTHER INFORMATION: n is a, c, g, or t

<400> SEQUENCE: 1
nnnnnnnnnn nn                                                          12

<210> SEQ ID NO 2
<211> LENGTH: 98
<212> TYPE: DNA
<213> ORGANISM: Artificial Sequence
<220> FEATURE:
<223> OTHER INFORMATION: Barcode Linker
<220> FEATURE:
<221> NAME/KEY: misc_feature
<222> LOCATION: (57)..(68)
<223> OTHER INFORMATION: n is a, c, g, or t

<400> SEQUENCE: 2
ccatctcatc cctgcgtgtc tccgactcag gcagtgaaaa aaaaaaaaaa aaaaaannnn       60
nnnnnnnnct gagactgcca aggcacacag gggatagg                              98

<210> SEQ ID NO 3
<211> LENGTH: 27
<212> TYPE: DNA
<213> ORGANISM: Artificial Sequence
<220> FEATURE:
<223> OTHER INFORMATION: Primer for emulsion PCR

<400> SEQUENCE: 3
cctatcccct gtgtgccttg gcagtct                                          27

<210> SEQ ID NO 4
<211> LENGTH: 25
<212> TYPE: DNA
<213> ORGANISM: Artificial Sequence
<220> FEATURE:
<223> OTHER INFORMATION: Primer for emulsion PCR

<400> SEQUENCE: 4
ccatctcatc cctgcgtgtc tccga                                            25

```
<210> SEQ ID NO 5
<211> LENGTH: 27
<212> TYPE: DNA
<213> ORGANISM: Artificial Sequence
<220> FEATURE:
<223> OTHER INFORMATION: Bio-F primer for PCR

<400> SEQUENCE: 5
cctatcccct gtgtgccttg gcagtct                                          27

<210> SEQ ID NO 6
<211> LENGTH: 34
<212> TYPE: DNA
<213> ORGANISM: Artificial Sequence
<220> FEATURE:
<223> OTHER INFORMATION: Solexa 3 adaptor-1 for Sequencing

<400> SEQUENCE: 6
gtgactggag ttcagacgtg tgctcttccg atct                                  34

<210> SEQ ID NO 7
<211> LENGTH: 34
<212> TYPE: DNA
<213> ORGANISM: Artificial Sequence
<220> FEATURE:
<223> OTHER INFORMATION: Solexa 3 adaptor-2 for Sequencing

<400> SEQUENCE: 7
agatcggaag agcacacgtc tgaactccag tcac                                  34

<210> SEQ ID NO 8
<211> LENGTH: 85
<212> TYPE: DNA
<213> ORGANISM: Artificial Sequence
<220> FEATURE:
<223> OTHER INFORMATION: Solexa primer for Sequencing

<400> SEQUENCE: 8
aatgatacgg cgaccaccga gatctacact ctttccctac acgacgctct tccgatctcc      60
tatcccctgt gtgccttggc agtct                                            85

<210> SEQ ID NO 9
<211> LENGTH: 43
<212> TYPE: DNA
<213> ORGANISM: Artificial Sequence
<220> FEATURE:
<223> OTHER INFORMATION: Index 1 primer for Sequencing

<400> SEQUENCE: 9
caagcagaag acggcatacg agatcgtgat gtgactggag ttc                        43

<210> SEQ ID NO 10
<211> LENGTH: 98
<212> TYPE: DNA
<213> ORGANISM: Artificial Sequence
<220> FEATURE:
<223> OTHER INFORMATION: Comprimentary Strand of Bardcode Linker
<220> FEATURE:
<221> NAME/KEY: misc_feature
<222> LOCATION: (31)..(42)
<223> OTHER INFORMATION: n is a, c, g, or t

<400> SEQUENCE: 10
cctatcccct gtgtgccttg gcagtctcag nnnnnnnnnn nntttttttt tttttttttt      60
ttcactgcct gagtcggaga cacgcaggga tgagatgg                              98
```

<210> SEQ ID NO 11
<211> LENGTH: 60
<212> TYPE: DNA
<213> ORGANISM: Artificial Sequence
<220> FEATURE:
<223> OTHER INFORMATION: Oligonucleotide cut by BstI
<220> FEATURE:
<221> NAME/KEY: misc_feature
<222> LOCATION: (19)..(30)
<223> OTHER INFORMATION: n is a, c, g, or t

<400> SEQUENCE: 11
aaaaaaaaaa aaaaaaaann nnnnnnnnnn ctgagactgc caaggcacac aggggatagg        60

<210> SEQ ID NO 12
<211> LENGTH: 62
<212> TYPE: DNA
<213> ORGANISM: Artificial Sequence
<220> FEATURE:
<223> OTHER INFORMATION: Oligonucleotide cut by BstI
<220> FEATURE:
<221> NAME/KEY: misc_feature
<222> LOCATION: (31)..(42)
<223> OTHER INFORMATION: n is a, c, g, or t

<400> SEQUENCE: 12
cctatcccct gtgtgccttg gcagtctcag nnnnnnnnnn nnttttttttt tttttttttt        60 tt                                                                      62

<210> SEQ ID NO 13
<211> LENGTH: 77
<212> TYPE: DNA
<213> ORGANISM: Artificial Sequence
<220> FEATURE:
<223> OTHER INFORMATION: Oligonucleotide attached to a bead

<400> SEQUENCE: 13
cagtttcagt cagttttta atttttttttt tttttttttt tcactgcctg agtcggagac        60
acgcagggat gagatgg                                                      77

<210> SEQ ID NO 14
<211> LENGTH: 64
<212> TYPE: DNA
<213> ORGANISM: Artificial Sequence
<220> FEATURE:
<223> OTHER INFORMATION: Oligonucleotide attached to a bead

<400> SEQUENCE: 14
cagactcagg gaagatcagg tttttttttt tttttttttt ccctgccgga atgccaaagc        60
ccac                                                                    64

<210> SEQ ID NO 15
<211> LENGTH: 70
<212> TYPE: DNA
<213> ORGANISM: Artificial Sequence
<220> FEATURE:
<223> OTHER INFORMATION: Oligonucleotide attached to a bead

<400> SEQUENCE: 15
cagactcagg gttttaacaa gtttttttt tttttttttt tcccggccaa acccgaaaac        60
ccccaagaaa                                                              70

<210> SEQ ID NO 16
<211> LENGTH: 58

<212> TYPE: DNA
<213> ORGANISM: Artificial Sequence
<220> FEATURE:
<223> OTHER INFORMATION: Oligonucleotide attached to a bead

<400> SEQUENCE: 16
cagtctcaga agttagaatg ttttttttttt ttttttgtttc actgcctcag tcggagac        58

<210> SEQ ID NO 17
<211> LENGTH: 60
<212> TYPE: DNA
<213> ORGANISM: Artificial Sequence
<220> FEATURE:
<223> OTHER INFORMATION: Oligonucleotide attached to a bead

<400> SEQUENCE: 17
cagtctcaga cattatattg tttttttttt tttttttttt cccggccgga gccgaaaacc        60

<210> SEQ ID NO 18
<211> LENGTH: 59
<212> TYPE: DNA
<213> ORGANISM: Artificial Sequence
<220> FEATURE:
<223> OTHER INFORMATION: Oligonucleotide attached to a bead

<400> SEQUENCE: 18
cagtctcaga cgggccttag tttttttttt tttttttttt ttcctggccg gattcgaaa        59

<210> SEQ ID NO 19
<211> LENGTH: 59
<212> TYPE: DNA
<213> ORGANISM: Artificial Sequence
<220> FEATURE:
<223> OTHER INFORMATION: Oligonucleotide attached to a bead

<400> SEQUENCE: 19
cagtctcagc actttcgggt tttttttttt tttttttttt ttatgcctga ttcgaaaac        59

<210> SEQ ID NO 20
<211> LENGTH: 58
<212> TYPE: DNA
<213> ORGANISM: Artificial Sequence
<220> FEATURE:
<223> OTHER INFORMATION: Oligonucleotide attached to a bead

<400> SEQUENCE: 20
cagtctcagc cggataactt gtttttttttt tttttttttt tcccggccgg attcgaaa        58

<210> SEQ ID NO 21
<211> LENGTH: 59
<212> TYPE: DNA
<213> ORGANISM: Artificial Sequence
<220> FEATURE:
<223> OTHER INFORMATION: Oligonucleotide attached to a bead

<400> SEQUENCE: 21
cagtctcagc tatcgtgcta gtttttttttt tttttttttt tccctgccgg agtcgaaaa        59

<210> SEQ ID NO 22
<211> LENGTH: 63
<212> TYPE: DNA
<213> ORGANISM: Artificial Sequence
<220> FEATURE:
<223> OTHER INFORMATION: Oligonucleotide attached to a bead

<400> SEQUENCE: 22

```
cagtctcagg accaggtctt cttttttttt ttttttttca cggccggagc cgaagacacc    60
agg                                                                  63

<210> SEQ ID NO 23
<211> LENGTH: 59
<212> TYPE: DNA
<213> ORGANISM: Artificial Sequence
<220> FEATURE:
<223> OTHER INFORMATION: Oligonucleotide attached to a bead

<400> SEQUENCE: 23
cagtctcagg gggagcgtac gttttttttt ttttttttc cctgcctgat tcgaaaaca     59

<210> SEQ ID NO 24
<211> LENGTH: 62
<212> TYPE: DNA
<213> ORGANISM: Artificial Sequence
<220> FEATURE:
<223> OTHER INFORMATION: Oligonucleotide attached to a bead

<400> SEQUENCE: 24
cagtctcagg tcattcaggt attttttttt tttttttttt cacggctgag ccgaaaacac    60
cc                                                                   62

<210> SEQ ID NO 25
<211> LENGTH: 60
<212> TYPE: DNA
<213> ORGANISM: Artificial Sequence
<220> FEATURE:
<223> OTHER INFORMATION: Oligonucleotide attached to a bead

<400> SEQUENCE: 25
cagtctcagt aaatgttagg gttttttttt ttttttttc ccggccggag tcgaaaaccc    60

<210> SEQ ID NO 26
<211> LENGTH: 59
<212> TYPE: DNA
<213> ORGANISM: Artificial Sequence
<220> FEATURE:
<223> OTHER INFORMATION: Oligonucleotide attached to a bead

<400> SEQUENCE: 26
cagtctcagt actggctatg attttttttt tttttttttt tccctgcctg attcaaaac    59

<210> SEQ ID NO 27
<211> LENGTH: 60
<212> TYPE: DNA
<213> ORGANISM: Artificial Sequence
<220> FEATURE:
<223> OTHER INFORMATION: Oligonucleotide attached to a bead

<400> SEQUENCE: 27
cagtctcagt aggggtcaat tttttttttt tttttttttt tttccccgct gattcgaaaa    60

<210> SEQ ID NO 28
<211> LENGTH: 60
<212> TYPE: DNA
<213> ORGANISM: Artificial Sequence
<220> FEATURE:
<223> OTHER INFORMATION: Oligonucleotide attached to a bead

<400> SEQUENCE: 28
cagtctcagt ggctaatctt gttttttttt ttttttttc ccggccggag tcggaaaccc    60
```

<210> SEQ ID NO 29
<211> LENGTH: 59
<212> TYPE: DNA
<213> ORGANISM: Artificial Sequence
<220> FEATURE:
<223> OTHER INFORMATION: Oligonucleotide attached to a bead

<400> SEQUENCE: 29
cagtctcagt ggctatcctc gttttttttt tttttttttt tcacggccgg atccgaaga      59

<210> SEQ ID NO 30
<211> LENGTH: 286
<212> TYPE: DNA
<213> ORGANISM: Artificial Sequence
<220> FEATURE:
<223> OTHER INFORMATION: Oligonucleotide having a barcode sequence and a
      nucleotide sequence drived from a cell

<400> SEQUENCE: 30
aatgatacgg cgaccaccga gatctacact ctttccctac acgacgctct tccgatctcc     60 tatccctgt gtgccttggc agtctcagct attcattctg tttttttttt tttttttttt     120
actttattaa aatactgagt tttatttcac atgtatattt ttgtctcccc accacttcca    180
tgtctgacca ccgctactac tatgtcctat cataacattc caagatcgga agagcacacg    240
tctgaactcc agtcacatca cgatctcgta tgccgtcttc tgcttg                   286

<210> SEQ ID NO 31
<211> LENGTH: 123
<212> TYPE: DNA
<213> ORGANISM: Artificial Sequence
<220> FEATURE:
<223> OTHER INFORMATION: Barcode Linker
<220> FEATURE:
<221> NAME/KEY: misc_feature
<222> LOCATION: (62)..(73)
<223> OTHER INFORMATION: n is a, c, g, or t

<400> SEQUENCE: 31
ccatctcatc cctgcgtgtc tccgactcag gcagtgaaaa aaaaaaaaa aaaaaaaaa        60 annnnnnnnn nnnacatagg ccgtcttcag ccgctgagac tgccaaggca cacaggggat    120
agg                                                                  123

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
cgtatcgcct ccctcgcgcc at                                              22

<210> SEQ ID NO 33
<211> LENGTH: 27
<212> TYPE: DNA
<213> ORGANISM: Artificial Sequence
<220> FEATURE:
<223> OTHER INFORMATION: primer

<400> SEQUENCE: 33
cctatcccct gtgtgccttg gcagtct                                         27

<210> SEQ ID NO 34
<211> LENGTH: 21

```
<212> TYPE: DNA
<213> ORGANISM: Artificial Sequence
<220> FEATURE:
<223> OTHER INFORMATION: primer

<400> SEQUENCE: 34
gcggctgaag acggcctatg t                                          21

<210> SEQ ID NO 35
<211> LENGTH: 12
<212> TYPE: DNA
<213> ORGANISM: Artificial Sequence
<220> FEATURE:
<223> OTHER INFORMATION: Barcode sequence

<400> SEQUENCE: 35
aacgtgcttg aa                                                    12

<210> SEQ ID NO 36
<211> LENGTH: 12
<212> TYPE: DNA
<213> ORGANISM: Artificial Sequence
<220> FEATURE:
<223> OTHER INFORMATION: Barcode sequence

<400> SEQUENCE: 36
acattggtct tg                                                    12

<210> SEQ ID NO 37
<211> LENGTH: 12
<212> TYPE: DNA
<213> ORGANISM: Artificial Sequence
<220> FEATURE:
<223> OTHER INFORMATION: Barcode sequence

<400> SEQUENCE: 37
agttccccga cc                                                    12

<210> SEQ ID NO 38
<211> LENGTH: 12
<212> TYPE: DNA
<213> ORGANISM: Artificial Sequence
<220> FEATURE:
<223> OTHER INFORMATION: Barcode sequence

<400> SEQUENCE: 38
cagaggaact ag                                                    12

<210> SEQ ID NO 39
<211> LENGTH: 12
<212> TYPE: DNA
<213> ORGANISM: Artificial Sequence
<220> FEATURE:
<223> OTHER INFORMATION: Barcode sequence

<400> SEQUENCE: 39
ccatggttta gg                                                    12

<210> SEQ ID NO 40
<211> LENGTH: 12
<212> TYPE: DNA
<213> ORGANISM: Artificial Sequence
<220> FEATURE:
<223> OTHER INFORMATION: Barcode sequence

<400> SEQUENCE: 40
```

```
cgtcaatctt tt                                                        12

<210> SEQ ID NO 41
<211> LENGTH: 12
<212> TYPE: DNA
<213> ORGANISM: Artificial Sequence
<220> FEATURE:
<223> OTHER INFORMATION: Barcode sequence

<400> SEQUENCE: 41
ctttatattt tt                                                        12

<210> SEQ ID NO 42
<211> LENGTH: 12
<212> TYPE: DNA
<213> ORGANISM: Artificial Sequence
<220> FEATURE:
<223> OTHER INFORMATION: Barcode sequence

<400> SEQUENCE: 42
gaagatcaga gt                                                        12

<210> SEQ ID NO 43
<211> LENGTH: 12
<212> TYPE: DNA
<213> ORGANISM: Artificial Sequence
<220> FEATURE:
<223> OTHER INFORMATION: Barcode sequence

<400> SEQUENCE: 43
gcagcttggg gt                                                        12

<210> SEQ ID NO 44
<211> LENGTH: 12
<212> TYPE: DNA
<213> ORGANISM: Artificial Sequence
<220> FEATURE:
<223> OTHER INFORMATION: Barcode sequence
<220> FEATURE:
<221> NAME/KEY: misc_feature
<222> LOCATION: (2)..(3)
<223> OTHER INFORMATION: n is a, c, g, or t

<400> SEQUENCE: 44
gnngttgcgg gt                                                        12

<210> SEQ ID NO 45
<211> LENGTH: 12
<212> TYPE: DNA
<213> ORGANISM: Artificial Sequence
<220> FEATURE:
<223> OTHER INFORMATION: Barcode sequence

<400> SEQUENCE: 45
gtaccctata tc                                                        12

<210> SEQ ID NO 46
<211> LENGTH: 12
<212> TYPE: DNA
<213> ORGANISM: Artificial Sequence
<220> FEATURE:
<223> OTHER INFORMATION: Barcode sequence

<400> SEQUENCE: 46
gtgctagtgg gg                                                        12
```

```
<210> SEQ ID NO 47
<211> LENGTH: 12
<212> TYPE: DNA
<213> ORGANISM: Artificial Sequence
<220> FEATURE:
<223> OTHER INFORMATION: Barcode sequence
<220> FEATURE:
<221> NAME/KEY: misc_feature
<222> LOCATION: (10)..(11)
<223> OTHER INFORMATION: n is a, c, g, or t

<400> SEQUENCE: 47
gtgctagtgn nt                                                          12

<210> SEQ ID NO 48
<211> LENGTH: 12
<212> TYPE: DNA
<213> ORGANISM: Artificial Sequence
<220> FEATURE:
<223> OTHER INFORMATION: Barcode sequence

<400> SEQUENCE: 48
gtgttcgtct tc                                                          12

<210> SEQ ID NO 49
<211> LENGTH: 12
<212> TYPE: DNA
<213> ORGANISM: Artificial Sequence
<220> FEATURE:
<223> OTHER INFORMATION: Barcode sequence

<400> SEQUENCE: 49
tagtttctgt ag                                                          12

<210> SEQ ID NO 50
<211> LENGTH: 12
<212> TYPE: DNA
<213> ORGANISM: Artificial Sequence
<220> FEATURE:
<223> OTHER INFORMATION: Barcode sequence

<400> SEQUENCE: 50
tatggagttt tg                                                          12

<210> SEQ ID NO 51
<211> LENGTH: 12
<212> TYPE: DNA
<213> ORGANISM: Artificial Sequence
<220> FEATURE:
<223> OTHER INFORMATION: Barcode sequence
<220> FEATURE:
<221> NAME/KEY: misc_feature
<222> LOCATION: (8)..(10)
<223> OTHER INFORMATION: n is a, c, g, or t

<400> SEQUENCE: 51
tcgaagtnnn at                                                          12

<210> SEQ ID NO 52
<211> LENGTH: 12
<212> TYPE: DNA
<213> ORGANISM: Artificial Sequence
<220> FEATURE:
<223> OTHER INFORMATION: Barcode sequence

<400> SEQUENCE: 52
tcgcacgcgg ta                                                          12
```

```
<210> SEQ ID NO 53
<211> LENGTH: 12
<212> TYPE: DNA
<213> ORGANISM: Artificial Sequence
<220> FEATURE:
<223> OTHER INFORMATION: Barcode sequence

<400> SEQUENCE: 53
tgaaccacgc gc                                                           12

<210> SEQ ID NO 54
<211> LENGTH: 12
<212> TYPE: DNA
<213> ORGANISM: Artificial Sequence
<220> FEATURE:
<223> OTHER INFORMATION: Barcode sequence

<400> SEQUENCE: 54
tgtgtcttaa cc                                                           12

<210> SEQ ID NO 55
<211> LENGTH: 12
<212> TYPE: DNA
<213> ORGANISM: Artificial Sequence
<220> FEATURE:
<223> OTHER INFORMATION: Barcode sequence

<400> SEQUENCE: 55
ttatagttcg tg                                                           12

<210> SEQ ID NO 56
<211> LENGTH: 12
<212> TYPE: DNA
<213> ORGANISM: Artificial Sequence
<220> FEATURE:
<223> OTHER INFORMATION: Barcode sequence

<400> SEQUENCE: 56
ttcctcggct at                                                           12

<210> SEQ ID NO 57
<211> LENGTH: 12
<212> TYPE: DNA
<213> ORGANISM: Artificial Sequence
<220> FEATURE:
<223> OTHER INFORMATION: Barcode sequence

<400> SEQUENCE: 57
ttcgaacagt aa                                                           12

<210> SEQ ID NO 58
<211> LENGTH: 12
<212> TYPE: DNA
<213> ORGANISM: Artificial Sequence
<220> FEATURE:
<223> OTHER INFORMATION: Barcode sequence

<400> SEQUENCE: 58
ttctttacca at                                                           12

<210> SEQ ID NO 59
<211> LENGTH: 12
<212> TYPE: DNA
<213> ORGANISM: Artificial Sequence
<220> FEATURE:
<223> OTHER INFORMATION: Barcode sequence
```

```
<400> SEQUENCE: 59
ttgttaggtt ac                                                      12

<210> SEQ ID NO 60
<211> LENGTH: 12
<212> TYPE: DNA
<213> ORGANISM: Artificial Sequence
<220> FEATURE:
<223> OTHER INFORMATION: Barcode sequence

<400> SEQUENCE: 60
ttgttgtccg tt                                                      12

<210> SEQ ID NO 61
<211> LENGTH: 12
<212> TYPE: DNA
<213> ORGANISM: Artificial Sequence
<220> FEATURE:
<223> OTHER INFORMATION: Barcode sequence

<400> SEQUENCE: 61
tttgaaagct gt                                                      12

<210> SEQ ID NO 62
<211> LENGTH: 12
<212> TYPE: DNA
<213> ORGANISM: Artificial Sequence
<220> FEATURE:
<223> OTHER INFORMATION: Barcode sequence

<400> SEQUENCE: 62
tttggagtca ga                                                      12

<210> SEQ ID NO 63
<211> LENGTH: 12
<212> TYPE: DNA
<213> ORGANISM: Artificial Sequence
<220> FEATURE:
<223> OTHER INFORMATION: Barcode sequence
<220> FEATURE:
<221> NAME/KEY: misc_feature
<222> LOCATION: (2)..(3)
<223> OTHER INFORMATION: n is a, c, g, or t

<400> SEQUENCE: 63
gnngttgcgg gt                                                      12

<210> SEQ ID NO 64
<211> LENGTH: 12
<212> TYPE: DNA
<213> ORGANISM: Artificial Sequence
<220> FEATURE:
<223> OTHER INFORMATION: Barcode sequence

<400> SEQUENCE: 64
tgtgtcttaa cc                                                      12

<210> SEQ ID NO 65
<211> LENGTH: 12
<212> TYPE: DNA
<213> ORGANISM: Artificial Sequence
<220> FEATURE:
<223> OTHER INFORMATION: Barcode sequence

<400> SEQUENCE: 65
```
acattggtct tg                                                       12

<210> SEQ ID NO 66
<211> LENGTH: 12
<212> TYPE: DNA
<213> ORGANISM: Artificial Sequence
<220> FEATURE:
<223> OTHER INFORMATION: Barcode sequence

<400> SEQUENCE: 66
ttctttacca at                                                       12

<210> SEQ ID NO 67
<211> LENGTH: 12
<212> TYPE: DNA
<213> ORGANISM: Artificial Sequence
<220> FEATURE:
<223> OTHER INFORMATION: Barcode sequence

<400> SEQUENCE: 67
tcgcacgcgg ta                                                       12

<210> SEQ ID NO 68
<211> LENGTH: 12
<212> TYPE: DNA
<213> ORGANISM: Artificial Sequence
<220> FEATURE:
<223> OTHER INFORMATION: Barcode sequence

<400> SEQUENCE: 68
ttcgaacagt aa                                                       12

<210> SEQ ID NO 69
<211> LENGTH: 12
<212> TYPE: DNA
<213> ORGANISM: Artificial Sequence
<220> FEATURE:
<223> OTHER INFORMATION: Barcode sequence

<400> SEQUENCE: 69
agttccccga cc                                                       12

<210> SEQ ID NO 70
<211> LENGTH: 12
<212> TYPE: DNA
<213> ORGANISM: Artificial Sequence
<220> FEATURE:
<223> OTHER INFORMATION: Barcode sequence

<400> SEQUENCE: 70
gtgttcgtct tc                                                       12

<210> SEQ ID NO 71
<211> LENGTH: 12
<212> TYPE: DNA
<213> ORGANISM: Artificial Sequence
<220> FEATURE:
<223> OTHER INFORMATION: Barcode sequence

<400> SEQUENCE: 71
ctttatattt tt                                                       12

<210> SEQ ID NO 72
<211> LENGTH: 12
<212> TYPE: DNA
<213> ORGANISM: Artificial Sequence

```
<220> FEATURE:
<223> OTHER INFORMATION: Barcode sequence

<400> SEQUENCE: 72
ccatggttta gg                                                            12

<210> SEQ ID NO 73
<211> LENGTH: 12
<212> TYPE: DNA
<213> ORGANISM: Artificial Sequence
<220> FEATURE:
<223> OTHER INFORMATION: Barcode sequence

<400> SEQUENCE: 73
gtgctagtgg gg                                                            12

<210> SEQ ID NO 74
<211> LENGTH: 12
<212> TYPE: DNA
<213> ORGANISM: Artificial Sequence
<220> FEATURE:
<223> OTHER INFORMATION: Barcode sequence

<400> SEQUENCE: 74
ttatagttcg tg                                                            12

<210> SEQ ID NO 75
<211> LENGTH: 12
<212> TYPE: DNA
<213> ORGANISM: Artificial Sequence
<220> FEATURE:
<223> OTHER INFORMATION: Barcode sequence

<400> SEQUENCE: 75
ttgttgtccg tt                                                            12

<210> SEQ ID NO 76
<211> LENGTH: 12
<212> TYPE: DNA
<213> ORGANISM: Artificial Sequence
<220> FEATURE:
<223> OTHER INFORMATION: Barcode sequence

<400> SEQUENCE: 76
cgtcaatctt tt                                                            12

<210> SEQ ID NO 77
<211> LENGTH: 12
<212> TYPE: DNA
<213> ORGANISM: Artificial Sequence
<220> FEATURE:
<223> OTHER INFORMATION: Barcode sequence

<400> SEQUENCE: 77
tagtttctgt ag                                                            12

<210> SEQ ID NO 78
<211> LENGTH: 12
<212> TYPE: DNA
<213> ORGANISM: Artificial Sequence
<220> FEATURE:
<223> OTHER INFORMATION: Barcode sequence

<400> SEQUENCE: 78
tgaaccacgc gc                                                            12
```

<210> SEQ ID NO 79
<211> LENGTH: 12
<212> TYPE: DNA
<213> ORGANISM: Artificial Sequence
<220> FEATURE:
<223> OTHER INFORMATION: Barcode sequence

<400> SEQUENCE: 79
ttgttaggtt ac                                                            12

<210> SEQ ID NO 80
<211> LENGTH: 12
<212> TYPE: DNA
<213> ORGANISM: Artificial Sequence
<220> FEATURE:
<223> OTHER INFORMATION: Barcode sequence

<400> SEQUENCE: 80
aacgtgcttg aa                                                            12

<210> SEQ ID NO 81
<211> LENGTH: 12
<212> TYPE: DNA
<213> ORGANISM: Artificial Sequence
<220> FEATURE:
<223> OTHER INFORMATION: Barcode sequence

<400> SEQUENCE: 81
cagaggaact ag                                                            12

<210> SEQ ID NO 82
<211> LENGTH: 12
<212> TYPE: DNA
<213> ORGANISM: Artificial Sequence
<220> FEATURE:
<223> OTHER INFORMATION: Barcode sequence
<220> FEATURE:
<221> NAME/KEY: misc_feature
<222> LOCATION: (8)..(10)
<223> OTHER INFORMATION: n is a, c, g, or t

<400> SEQUENCE: 82
tcgaagtnnn at                                                            12

<210> SEQ ID NO 83
<211> LENGTH: 12
<212> TYPE: DNA
<213> ORGANISM: Artificial Sequence
<220> FEATURE:
<223> OTHER INFORMATION: Barcode sequence

<400> SEQUENCE: 83
gtaccctata tc                                                            12

<210> SEQ ID NO 84
<211> LENGTH: 12
<212> TYPE: DNA
<213> ORGANISM: Artificial Sequence
<220> FEATURE:
<223> OTHER INFORMATION: Barcode sequence
<220> FEATURE:
<221> NAME/KEY: misc_feature
<222> LOCATION: (10)..(11)
<223> OTHER INFORMATION: n is a, c, g, or t

<400> SEQUENCE: 84
gtgctagtgn nt                                                            12

<210> SEQ ID NO 85
<211> LENGTH: 12
<212> TYPE: DNA
<213> ORGANISM: Artificial Sequence
<220> FEATURE:
<223> OTHER INFORMATION: Barcode sequence

<400> SEQUENCE: 85
gcagcttggg gt                                                                12

<210> SEQ ID NO 86
<211> LENGTH: 12
<212> TYPE: DNA
<213> ORGANISM: Artificial Sequence
<220> FEATURE:
<223> OTHER INFORMATION: Barcode sequence

<400> SEQUENCE: 86
tatggagttt tg                                                                12

<210> SEQ ID NO 87
<211> LENGTH: 12
<212> TYPE: DNA
<213> ORGANISM: Artificial Sequence
<220> FEATURE:
<223> OTHER INFORMATION: Barcode sequence

<400> SEQUENCE: 87
tttggagtca ga                                                                12

<210> SEQ ID NO 88
<211> LENGTH: 12
<212> TYPE: DNA
<213> ORGANISM: Artificial Sequence
<220> FEATURE:
<223> OTHER INFORMATION: Barcode sequence

<400> SEQUENCE: 88
tttgaaagct gt                                                                12

<210> SEQ ID NO 89
<211> LENGTH: 12
<212> TYPE: DNA
<213> ORGANISM: Artificial Sequence
<220> FEATURE:
<223> OTHER INFORMATION: Barcode sequence

<400> SEQUENCE: 89
ttcctcggct at                                                                12

<210> SEQ ID NO 90
<211> LENGTH: 12
<212> TYPE: DNA
<213> ORGANISM: Artificial Sequence
<220> FEATURE:
<223> OTHER INFORMATION: Barcode sequence

<400> SEQUENCE: 90
ttctttacca at                                                                12

<210> SEQ ID NO 91
<211> LENGTH: 12
<212> TYPE: DNA
<213> ORGANISM: Artificial Sequence
<220> FEATURE:

<223> OTHER INFORMATION: Barcode sequence

<400> SEQUENCE: 91
gaagatcaga gt                                                              12

<210> SEQ ID NO 92
<211> LENGTH: 12
<212> TYPE: DNA
<213> ORGANISM: Artificial Sequence
<220> FEATURE:
<223> OTHER INFORMATION: Barcode sequence

<400> SEQUENCE: 92
aggtcaaagg at                                                              12

<210> SEQ ID NO 93
<211> LENGTH: 12
<212> TYPE: DNA
<213> ORGANISM: Artificial Sequence
<220> FEATURE:
<223> OTHER INFORMATION: Barcode sequence

<400> SEQUENCE: 93
tctcataatg tt                                                              12

<210> SEQ ID NO 94
<211> LENGTH: 12
<212> TYPE: DNA
<213> ORGANISM: Artificial Sequence
<220> FEATURE:
<223> OTHER INFORMATION: Barcode sequence

<400> SEQUENCE: 94
gtagcgcgct tt                                                              12

<210> SEQ ID NO 95
<211> LENGTH: 12
<212> TYPE: DNA
<213> ORGANISM: Artificial Sequence
<220> FEATURE:
<223> OTHER INFORMATION: Barcode sequence

<400> SEQUENCE: 95
aattctgatg ct                                                              12

<210> SEQ ID NO 96
<211> LENGTH: 12
<212> TYPE: DNA
<213> ORGANISM: Artificial Sequence
<220> FEATURE:
<223> OTHER INFORMATION: Barcode sequence

<400> SEQUENCE: 96
ttttgttgta tc                                                              12

<210> SEQ ID NO 97
<211> LENGTH: 12
<212> TYPE: DNA
<213> ORGANISM: Artificial Sequence
<220> FEATURE:
<223> OTHER INFORMATION: Barcode sequence

<400> SEQUENCE: 97
gctatcgatt at                                                              12

```
<210> SEQ ID NO 98
<211> LENGTH: 12
<212> TYPE: DNA
<213> ORGANISM: Artificial Sequence
<220> FEATURE:
<223> OTHER INFORMATION: Barcode sequence

<400> SEQUENCE: 98
tttacctgag gg                                                             12

<210> SEQ ID NO 99
<211> LENGTH: 12
<212> TYPE: DNA
<213> ORGANISM: Artificial Sequence
<220> FEATURE:
<223> OTHER INFORMATION: Barcode sequence

<400> SEQUENCE: 99
ttacccgttt gg                                                             12

<210> SEQ ID NO 100
<211> LENGTH: 12
<212> TYPE: DNA
<213> ORGANISM: Artificial Sequence
<220> FEATURE:
<223> OTHER INFORMATION: Barcode sequence

<400> SEQUENCE: 100
ttcattctct ct                                                             12

<210> SEQ ID NO 101
<211> LENGTH: 12
<212> TYPE: DNA
<213> ORGANISM: Artificial Sequence
<220> FEATURE:
<223> OTHER INFORMATION: Barcode sequence

<400> SEQUENCE: 101
gtctcaggtt cc                                                             12

<210> SEQ ID NO 102
<211> LENGTH: 12
<212> TYPE: DNA
<213> ORGANISM: Artificial Sequence
<220> FEATURE:
<223> OTHER INFORMATION: Barcode sequence

<400> SEQUENCE: 102
tactgttaat tt                                                             12

<210> SEQ ID NO 103
<211> LENGTH: 12
<212> TYPE: DNA
<213> ORGANISM: Artificial Sequence
<220> FEATURE:
<223> OTHER INFORMATION: Barcode sequence

<400> SEQUENCE: 103
tcttctgatt aa                                                             12

<210> SEQ ID NO 104
<211> LENGTH: 12
<212> TYPE: DNA
<213> ORGANISM: Artificial Sequence
<220> FEATURE:
<223> OTHER INFORMATION: Barcode sequence
```

```
<400> SEQUENCE: 104
gttttcttcg at                                                          12

<210> SEQ ID NO 105
<211> LENGTH: 12
<212> TYPE: DNA
<213> ORGANISM: Artificial Sequence
<220> FEATURE:
<223> OTHER INFORMATION: Barcode sequence

<400> SEQUENCE: 105
tggcttcaga ta                                                          12

<210> SEQ ID NO 106
<211> LENGTH: 12
<212> TYPE: DNA
<213> ORGANISM: Artificial Sequence
<220> FEATURE:
<223> OTHER INFORMATION: Barcode sequence

<400> SEQUENCE: 106
tgttttttta ag                                                          12

<210> SEQ ID NO 107
<211> LENGTH: 12
<212> TYPE: DNA
<213> ORGANISM: Artificial Sequence
<220> FEATURE:
<223> OTHER INFORMATION: Barcode sequence

<400> SEQUENCE: 107
aatggaaggc ta                                                          12

<210> SEQ ID NO 108
<211> LENGTH: 12
<212> TYPE: DNA
<213> ORGANISM: Artificial Sequence
<220> FEATURE:
<223> OTHER INFORMATION: Barcode sequence

<400> SEQUENCE: 108
cttgctctat tg                                                          12

<210> SEQ ID NO 109
<211> LENGTH: 12
<212> TYPE: DNA
<213> ORGANISM: Artificial Sequence
<220> FEATURE:
<223> OTHER INFORMATION: Barcode sequence

<400> SEQUENCE: 109
acgattgatc tt                                                          12

<210> SEQ ID NO 110
<211> LENGTH: 12
<212> TYPE: DNA
<213> ORGANISM: Artificial Sequence
<220> FEATURE:
<223> OTHER INFORMATION: Barcode sequence

<400> SEQUENCE: 110
agaataggaa ta                                                          12

<210> SEQ ID NO 111
<211> LENGTH: 12
```

```
<212> TYPE: DNA
<213> ORGANISM: Artificial Sequence
<220> FEATURE:
<223> OTHER INFORMATION: Barcode sequence

<400> SEQUENCE: 111
ctgtactgcg ta                                                              12
```

METHOD FOR ANALYZING NUCLEIC ACID DERIVED FROM SINGLE CELL

TECHNICAL FIELD

The present application is a National Stage Application of PCT/JP2015/060841, filed Apr. 7, 2015, which claims priority from Japanese Patent Application No. 2014-095011, which are incorporated herein by reference.

The present invention relates to: a method of producing a bead having bound thereto oligonucleotides each having one kind of barcode sequence and configured to analyze a composition of nucleic acids derived from a single cell; a bead produced by the production method; a microplate having the bead arranged in a reaction well; and a method of analyzing a composition of nucleic acids derived from a single cell using the bead or the microplate.

BACKGROUND ART

A cell is the minimum unit from the viewpoints of functions and structures of organisms. However, an attempt has heretofore been made to investigate, for example, the functions and structures of organisms only for cell populations, but for example, the kinds of substances produced by individual cells have been poorly investigated. The current biological findings are not findings obtained from individual cells but findings obtained from cell populations. Recent investigations have revealed that gene expressions in different cells are diverse even when the cells are obviously similar types (for example, cancer tissues), and it is desired to investigate features, such as gene expression, in each cell.

A human immune system includes T cells, and the T cells include Th2 cells. The Th2 cells are known to produce cytokines, such as IL-4, IL-5, and IL-6. However, previous investigations have not revealed, for example, whether individual cells always produce all of the cytokines at a constant ratio, whether the ratio of the cytokines produced varies according to circumstances, whether cells each producing a part of the cytokines gather to seem to produce all the cytokines when observed as a population, and how the cytokines are produced, and at the same time, what kinds of receptors and transcription factors are produced. Cells are greatly affected by a microenvironment, respond differently by a small number of molecules involved in transcription and translation, and produce probabilistic responses to some extent, and hence expression responses of individual cells are considered to be different from each other.

There are known some methods each involving preparing a double-stranded cDNA using RNA derived from one eukaryotic cell or using a minute amount of RNA that is almost the same as the amount of the RNA derived from one eukaryotic cell, specifically, using about 10 pg of total RNA as a material, and analyzing gene expressions using the cDNA (Non Patent Literature 1 and Non Patent Literature 2). In addition, it is assumed that at a minimum, only one molecule (one copy) of a transcript derived from one cell is present, and hence a device capable of sequencing one nucleic acid molecule has been developed. However, in actuality, the device has the following problems: the device requires use of hundreds of cells, provides low accuracy, and can detect only about 20% of expressed mRNAs.

Accordingly, in order to detect a transcript derived from one cell, it is necessary to increase the amount of the transcript by amplification in advance. As means for amplifying the transcript derived from one cell, there is given means involving solubilizing one cell to separate mRNAs, synthesizing cDNAs using oligo(dT) or random primers, and amplifying the cDNAs by PCR or in vitro transcription (IVT). The use of the PCR has a problem in that not only the amount of the transcript amplified but also the amount of non-specific by-products is large. The cDNAs derived from the mRNAs have various lengths, and it is extremely difficult to amplify fragments having various lengths by PCR without losing a quantification property. In addition, the amount of fragments amplified becomes larger by increasing the number of PCR reaction cycles. However, when a sample includes an extremely high level of cDNAs of a transcript before amplification (for example, tens of thousands of copies are present per cell) and an extremely low level of cDNAs of a transcript (for example, one copy is present per cell), an increase in number of the PCR reaction cycles may lead to a reduction in amplification efficiency of the cDNAs present in a high level. Thus, the presence ratio of the amplified products in all of the resultant amplified products may not reflect the ratio of transcripts in the cell. In addition, IVT has an advantage in that non-specific by-products are produced only in a small amount, but has problems in that cRNA having a length of 1 kb or more is hardly acquired, in that the method requires time and additional work, and in that the amplification amount is not so large. In addition, those methods require treatments for individual cells, and require time and additional work, and hence the number of cells measured is restricted.

As a method of detecting a transcript derived from one cell, there has been proposed a method involving using a bead having bound thereto an oligonucleotide having a barcode sequence (Patent Literature 1). In Patent Literature 1, there is a disclosure of SEQ ID NO: 9 as a specific oligonucleotide bound to a bead, but the oligonucleotide represented by SEQ ID NO: 9 does not have a sequence in which an oligo(dT) is exposed at the 3' end.

CITATION LIST

Patent Literature

[PTL 1] US 2013/0274117 A1

Non Patent Literature

[NPL 1] Development and applications of single-cell transcriptome analysis. Tang F, Lao K, Surani M A. Nat Methods. 2011 April; 8 (4 Suppl): S6-11.
[NPL 2] Review, Single cell genomics: advances and future perspectives. Macaulay I C, Voet T. PLoS Genet. 2014, 10(1): e1004126

SUMMARY OF INVENTION

Technical Problem

An object of the present invention is to provide means for efficiently collecting nucleic acids from a single cell and means for analyzing the nucleic acids collected.

Solution to Problem

The inventors of the present invention have made extensive investigations, and as a result, have found that a double-stranded oligonucleotide bound to a bead may be treated with a restriction enzyme to arrange a nucleic acid capture sequence at the 3' end, and have focused on the fact that a restriction enzyme recognition sequence is arranged on the 3' side of the nucleic acid capture sequence in a barcode linker that serves as a template for amplification of the oligonucleotide on the bead. Thus, the present invention has been achieved.

The inventors have further made extensive investigations on a method of analyzing nucleic acids derived from a single cell using a bead having bound thereto single-stranded oligonucleotides, and as a result, have found that the nucleic acids derived from a single cell can be easily and comprehensively analyzed by compositely combining a plurality of technologies each involving inoculating cells onto a microplate having one bead arranged in one reaction well. Thus, the present invention has been achieved.

That is, the present invention is as described below.

1. A microplate for use in a method of analyzing a composition of nucleic acids derived from a single cell, the microplate including a plurality of reaction wells, the microplate having one bead arranged in one reaction well, the one bead having bound thereto a plurality of molecules of single-stranded oligonucleotides, the single-stranded oligonucleotides each having a nucleic acid capture sequence exposed at a 3' end and a barcode sequence on a 5' side of the nucleic acid capture sequence, the barcode sequence including a base sequence that differs from bead to bead.

2. A microplate according to Item 1, in which the one bead is arranged in each of 80% or more of the reaction wells of the microplate.

3. A microplate according to Item 1 or 2, in which the bead has a size of from 20 μm to 40 μm.

4. A method of producing the microplate of any one of Items 1 to 3, the method including the following steps:

(a) preparing a microplate including a plurality of reaction wells;

(b) adding, onto the microplate, beads that satisfy a ratio of a diameter of each reaction well to a diameter of each bead of from 1.2 to 1.75; and (c) arranging one bead in one reaction well by covering the microplate with a semipermeable membrane and squeezing a surface of the microplate with a pressing member.

5. A reagent kit for use in a method of analyzing a composition of nucleic acids derived from a single cell, the reagent kit including the microplate of any one of Items 1 to 3 and a nucleic acid extraction reagent.

6. A method of analyzing a composition of nucleic acids derived from a single cell using the microplate including a plurality of reaction wells of any one of Items 1 to 3, the microplate having one bead arranged in one reaction well, the one bead having bound thereto a plurality of molecules of single-stranded oligonucleotides, the single-stranded oligonucleotides each having a nucleic acid capture sequence exposed at a 3' end and a barcode sequence on a 5' side of the nucleic acid capture sequence, the barcode sequence including a base sequence that differs from bead to bead, the method including the following steps:

(1) capturing, after inoculating cells onto the microplate to arrange one cell in one reaction well and extracting nucleic acids from the cell in the reaction well of the microplate, the nucleic acids derived from the cell by single-stranded oligonucleotides on the bead;

(2) performing a nucleic acid amplification reaction using, as templates, the nucleic acids captured by the single-stranded oligonucleotides on the bead to produce amplified fragments; and (3) determining barcode sequences in the resultant amplified fragments to identify fragments having the same barcode sequence as fragments derived from the same cell.

7. A method of analyzing a composition of nucleic acids derived from a single cell using the microplate including a plurality of reaction wells of any one of Items 1 to 3, the microplate having one bead arranged in one reaction well, the one bead having bound thereto a plurality of molecules of single-stranded oligonucleotides, the single-stranded oligonucleotides each having a nucleic acid capture sequence exposed at a 3' end and a barcode sequence on a 5' side of the nucleic acid capture sequence, the barcode sequence including a base sequence that differs from bead to bead, the method including the following steps:

(1) preparing a plurality of beads obtained by capturing nucleic acids derived from a single cell by single-stranded oligonucleotides on each bead;

(2) performing a nucleic acid amplification reaction using, as templates, the nucleic acids captured by the single-stranded oligonucleotides on the bead to produce amplified fragments; and (3) determining barcode sequences in the resultant amplified fragments to identify fragments having the same barcode sequence as fragments derived from the same cell.

8. An analysis method according to Item 6 or 7, in which the capturing step serving as the step (1) of Item 6 includes the following steps, or the beads obtained by capturing nucleic acids by single-stranded oligonucleotides in the step (1) of Item 7 are prepared by the following steps:

(1-1) inoculating cells onto the microplate to arrange one cell in one reaction well, followed by covering of the microplate with a semipermeable membrane;

(1-2) extracting nucleic acids from the cell by adding a nucleic acid extraction reagent from above the semipermeable membrane to dissolve the cell in the reaction well; and (1-3) capturing the nucleic acids extracted from the cell by the single-stranded oligonucleotides on the bead.

9. An analysis method according to Item 8, further including, after the step (1-3) of Item 8, collecting the beads arranged in the reaction wells of the microplate and having captured nucleic acids in one container to collect the nucleic acids derived from a plurality of cells in the one container.

10. An analysis method according to any one of Items 6 to 9, in which the nucleic acids derived from the cell include mRNAs, the nucleic acid capture sequence in the oligonucleotide on the bead includes an oligo(dT) sequence, and the step (2) of Item 6 or 7 further includes performing a reverse transcription reaction before the nucleic acid amplification reaction.

11. A method of producing a bead, the bead having bound thereto a plurality of molecules of single-stranded oligonucleotides, the single-stranded oligonucleotides each having a nucleic acid capture sequence exposed at a 3' end and a barcode sequence on a 5' side of the nucleic acid capture sequence, the barcode sequence including a base sequence that differs from bead to bead, the method including the following steps:

(i) performing a nucleic acid amplification reaction using, as a template, a barcode linker having a barcode sequence, a nucleic acid capture sequence, and a restriction enzyme recognition sequence in a droplet including one bead to bind a double-stranded oligonucleotide serving as an amplified product to the bead, the barcode linker having the restriction enzyme recognition sequence adjacently to a 3' side of the nucleic acid capture sequence;

(ii) after the nucleic acid amplification reaction of the step (i), subjecting the double-stranded oligonucleotide bound onto the bead to restriction enzyme treatment to expose the nucleic acid capture sequence at a 3' end of the double-stranded oligonucleotide; and (iii) denaturing the double-stranded oligonucleotide bound onto the bead into a single-stranded oligonucleotide.

12. A bead, which is produced by the method of producing a bead of Item 11.

13. A method of analyzing a composition of nucleic acids derived from a single cell using the bead of Item 12, the method including the following steps (1) to (3):

(1) extracting, under a state in which one bead is brought into contact with one cell in a single compartment, nucleic acids from the cell, followed by binding of the nucleic acids derived from the cell to single-stranded oligonucleotides on the bead;

(2) performing a nucleic acid amplification reaction using, as templates, the nucleic acids bound to the single-stranded oligonucleotide on the bead to produce amplified fragments; and (3) determining barcode sequences in the resultant amplified fragments to identify fragments having the same barcode sequence as fragments derived from the same cell.

Advantageous Effects of Invention

According to the method of manufacturing (producing) a bead of the present invention, a bead having bound thereto oligonucleotides each having a nucleic acid capture sequence exposed at the 3' end can be manufactured easily. The bead obtained by the manufacturing method of the present invention is a bead having bound thereto oligonucleotides each having one kind of barcode sequence, and can collect a minute amount of nucleic acids derived from a single cell for a gene analysis. The bead can capture nucleic acids efficiently because the nucleic acid capture sequence is exposed at the 3' end of each oligonucleotide. In addition, according to the method of manufacturing a bead of the present invention, many beads each having a single barcode sequence can be easily produced because a nucleic acid having one kind of barcode sequence is amplified in a droplet including one bead.

In addition, according to the analysis method of the present invention, nucleic acids derived from a single cell can be easily and comprehensively analyzed. According to the analysis method of the present invention, the composition, such as the kinds or amounts, of nucleic acids in a single cell can be analyzed accurately. For example, the nucleic acids can be collected and analyzed while the quantitative ratio of the genes in a single cell is maintained. When the nucleic acids are mRNAs, the expression ratio of various genes in total RNA in one cell can be determined by the present invention. Further, the present invention can exhaustively reveal details of not only a small number of genes or a predetermined gene but also expressed genes. Accordingly, the present invention can be used for a transcriptome analysis for each of hundreds to tens of thousands of cells. When beads having bound thereto oligonucleotides each having a barcode sequence are used, the barcode sequence may be added to nucleic acids derived from each cell to omit treatment of the respective cells. As a result, transcripts of many cells can be analyzed quickly, easily, and inexpensively.

In addition, according to the microplate of the present invention, capture of nucleic acids derived from a single cell and an analysis of a nucleic acid amplification reaction or the like can be performed in different locations, and hence the number of samples to be analyzed may increase drastically.

BRIEF DESCRIPTION OF DRAWINGS

FIG. 1A is a diagram for illustrating a method of manufacturing a bead of the present invention (Example 1).

FIG. 1B is a diagram for illustrating a method of analyzing nucleic acids derived from a single cell using a bead of the present invention (Example 2).

FIG. 2 is a figure for showing results of determination of base sequences of oligonucleotides on beads obtained by the method of manufacturing a bead of the present invention (Example 1).

FIG. 3 is a figure for showing a result of confirmation of the fact that a barcode sequence can be added to a nucleic acid derived from a single cell using a bead obtained by the method of manufacturing a bead of the present invention (Example 2).

FIG. 4 is a table for showing results of confirmation of the fact that barcode sequences can be added to nucleic acids derived from a single cell using a microplate of the present invention (Example 4).

FIG. 5 is a table for showing the numbers of genes and the total numbers of reads determined by an analysis on gene expression of a hepatocellular carcinoma cell line using the microplate of the present invention (Example 5).

FIG. 6 is a table for showing names of genes identified by barcode sequences and confirmed to be expressed in respective cells, and the numbers of reads, determined by an analysis for the hepatocellular carcinoma cell line using the microplate of the present invention (Example 5).

FIG. 7 is a graph for showing a correlation between the kinds of genes and the number of reads per cell, the correlation being determined by the analysis for the hepatocellular carcinoma cell line using the microplate of the present invention (Example 5).

FIG. 8 is a graph for showing correlations of gene frequencies per cell between two cells, the correlations being determined by the analysis for the hepatocellular carcinoma cell line using the microplate of the present invention (Example 5).

FIG. 9 is a photograph for showing the microplate of the present invention in which beads are arranged in reaction wells (Example 3).

DESCRIPTION OF EMBODIMENTS

The present invention relates to a method of producing a bead having bound thereto single-stranded oligonucleotides each having a barcode sequence and configured to analyze the composition of nucleic acids derived from a single cell. Each of the oligonucleotides has a nucleic acid capture sequence capable of being bound to a nucleic acid derived from a single cell. When each single-stranded oligonucleotide on the bead is bound to a nucleic acid derived from a single cell by the nucleic acid capture sequence, the nucleic acid is bound onto the bead. The nucleic acids can be collected by collecting beads having bound thereto the nucleic acids.

The bead of the present invention may be produced by a method involving the following steps:

(i) performing a nucleic acid amplification reaction using, as a template, a barcode linker having one kind of barcode sequence, a nucleic acid capture sequence, and a restriction enzyme recognition sequence in a droplet including one bead to bind a double-stranded oligonucleotide having the barcode sequence to the bead, the barcode linker having the restriction enzyme recognition sequence adjacently to the 3' side of the nucleic acid capture sequence;

(ii) after the nucleic acid amplification reaction of the step (i), subjecting the double-stranded oligonucleotide bound onto the bead to restriction enzyme treatment to expose the nucleic acid capture sequence at the 3' end of the double-stranded oligonucleotide; and (iii) denaturing the double-stranded oligonucleotide bound onto the bead into a single-stranded oligonucleotide.

In the present invention, the term "barcode sequence" refers to a random base sequence including A (adenine), G (guanine), C (cytosine), and T (thymine). When labeling with different barcode sequences is performed in respective cells, nucleic acids derived from the cells can be identified. The labeling with a barcode sequence may be performed by adding one kind of barcode sequence to nucleic acids derived from a single cell. The barcode sequence has a length of preferably from 10 bases to 25 bases. For example, in the case where the barcode sequence has a length of 12 bases, the barcode sequence may be represented as NNNNNNNNNNNN (SEQ ID NO: 1). In this case, nucleic acids having $4^{12}$ kinds of diverse barcode sequences can be amplified at one time, and $4^{12}$ kinds of beads can be produced.

In the present invention, the term "nucleic acid capture sequence" refers to a sequence capable of being bound to (hybridized with) nucleic acids derived from a cell. The nucleic acids derived from a cell may be genomic DNAs or mRNAs. When the nucleic acids are mRNAs, the nucleic acid capture sequence is preferably an oligo(dT) including T. The oligo(dT) may have any length as long as it can anneal with (hybridize with) a poly(A) tail of mRNA. The bead produced by the present invention can be used for analyzing genomic DNAs derived from a cell. For example, when DNA coding for an antibody is analyzed, the nucleic acid capture sequence may be selected from base sequences each coding for a region having a relatively small change, such as a constant region of the antibody. When DNAs in the cell are collected with the nucleic acid capture sequence, the kind of antibody produced in each cell, HLA type, and the like can be analyzed (DeKosky B J1 et al., Nat Biotechnol. 2013 February; 31 (2): 166-9. doi: 10.1038/nbt.2492. Epub 2013 Jan. 20).

In the present invention, the "restriction enzyme recognition sequence" is a sequence that may be recognized and cleaved with a restriction enzyme, and may be selected depending on the kind of restriction enzyme to be used.

The barcode linker used in the step (1) has a barcode sequence, a nucleic acid capture sequence, and a restriction enzyme recognition sequence, or has complementary sequences thereof. The barcode linker preferably has a nucleic acid capture sequence adjacently to the 3' side of the barcode sequence, and a restriction enzyme recognition sequence adjacently to the 3' side of the nucleic acid capture sequence. When the barcode linker has a sequence complementary to a barcode sequence or the like, the barcode linker has a nucleic acid capture sequence adjacently to the 5' side of the barcode sequence, and a restriction enzyme recognition sequence adjacently to the 5' side of the nucleic acid capture sequence. The barcode linker is an oligonucleotide that is used to bind an oligonucleotide having a barcode sequence and a nucleic acid capture sequence onto a bead. Specifically, a nucleic acid amplification reaction is performed using the barcode linker as a template in a droplet including one bead. In general, the nucleic acid amplification reaction is referred to as emulsion PCR. The reaction may be performed in a water-in-oil droplet, and may be performed using a kit, such as GS Junior Titanium emPCR Kit (Lib-L). The barcode linker preferably has primer complementary sequences for annealing primers in the nucleic acid amplification reaction. The primer complementary sequences are located so as to sandwich a base sequence including the nucleic acid capture sequence and the restriction enzyme recognition sequence.

The barcode linker may have any sequence, and for example, the following sequence may be given.

(SEQ ID NO: 2)
5'-CCATCTCATCCCTGCGTGTCTCCGACTCAGGCAGTGAAAAAAAA

AAAAAAAAAAANNNNNNNNNNNNCTGAGACTGCCAAGGCACACAGGGG

ATAGG-3'

In the base sequence, the base sequence at positions 1 to 25 from the 5' end is a primer complementary sequence, the base sequence NNNNNNNNNNNN (SEQ ID NO: 1) at positions 57 to 68 is a barcode sequence, the poly(dA) sequence (a sequence complementary to an oligo(dT) sequence) at positions 37 to 56 is a nucleic acid capture sequence, the base sequence at positions 31 to 36 is a restriction enzyme recognition sequence, and the base sequence at positions 72 to 98 is a primer complementary sequence.

In addition, the following sequence may be adopted as the sequence of the barcode linker.

(SEQ ID NO: 31):
5'-CCATCTCATCCCTGCGTGTCTCCGACTCAG<u>GCAGTG</u>AAAAAAAA

AAAAAAAAAAAAAAANNNNNNNNNNNNA<u>CATAGGCCGTCTTCAGCCG</u>

CTGAGACTGCCAAGGCACACAGGGGATAGG-3'

In the base sequence, the base sequence at positions 1 to 25 from the 5' end is a primer complementary sequence, the base sequence at positions 31 to 36 is a restriction enzyme recognition sequence, the poly(dA) sequence at positions 37 to 61 is a nucleic acid capture sequence, the base sequence at positions 62 to 73, NNNNNNNNNNNN (SEQ ID NO: 1), is a barcode sequence, and the base sequence at positions 97 to 123 is a primer complementary sequence. The base sequence at positions 75 to 93 is any base sequence, and may be used in an analysis of nucleic acids derived from a cell using a bead as a primer complementary sequence for amplification of the nucleic acid after the nucleic acids derived from the cell are captured.

When the nucleic acid amplification reaction in the step (i) is PCR, in the PCR, three steps, i.e., a step of thermally denaturing double-stranded DNA into single-stranded DNAs, a step of binding primers to the single-stranded DNAs, and a step of elongating the DNAs with a DNA polymerase are repeated as one PCR cycle to amplify a nucleic acid of interest. In PCR in the step (i), the PCR cycle is preferably repeated 40 times to 60 times. This can bind millions of, preferably $10^6$ to $8 \times 10^6$ oligonucleotide molecules each having a barcode sequence onto the bead. When emulsion PCR is performed in the step (i), PCR is performed in a droplet including one bead. Accordingly, the barcode sequences in the oligonucleotides bound to one bead are identical. One bead and one kind of barcode linker (preferably one barcode linker molecule) are allowed to react in one droplet, and hence a ratio between the number of beads and the number of barcode linker molecules can be adjusted appropriately. The case where the number of barcode linker molecules relative to the number of beads is too large is not preferred because different kinds of barcode linkers may be redundantly bound to one bead, and the case where the number of barcode linker molecules relative to the number of beads is too small is not preferred because production efficiency of beads having bound thereto oligonucleotides is low. For example, when the barcode linker has a base sequence represented by SEQ ID NO: 2, $10 \times 10^5$ to $10 \times 10^6$ barcode linker molecules are preferably mixed with $10 \times 10^6$ beads. In typical emulsion PCR, an emulsion is prepared using a mixer, but a device based on fluid engineering is preferably used to more appropriately adjust the ratio between the number of beads in a droplet and the number of barcode linker molecules. For example, a device having a plurality of flow paths each having a width 1.5 times to 5.0 times as large as the diameter of a bead and being integrated at the exit may be used to produce a droplet including one bead and one kind of barcode linker.

A forward primer obtained by adding biotin to the 5' end is preferably used as the primer used for PCR in the step (i). After amplification by PCR, biotin is bound to the 5' ends of amplified products, and hence beads having bound thereto the amplified products can be easily purified by using a carrier (for example, a magnetic material, such as a magnetic bead) bound to avidin.

In the step (ii), the double-stranded oligonucleotide bound onto the bead by the nucleic acid amplification reaction is treated with a restriction enzyme. The restriction enzyme recognition sequence is located adjacently to the 3' side of the nucleic acid capture sequence in the barcode linker. When the double-stranded oligonucleotide is treated with a restriction enzyme in the step (2), the nucleic acid capture sequence can be exposed at the 3' end of the double-stranded oligonucleotide on the bead (the outside end not bound onto the bead). Any kind of restriction enzyme may be used as long as the enzyme can recognize a restriction enzyme recognition sequence, and examples thereof include restriction enzymes such as BtsI.

In the step (iii), the double-stranded oligonucleotide bound onto the bead is denatured into a single-stranded oligonucleotide. Denaturation of the oligonucleotide may be performed by a method known per se, and for example, there may be given alkali treatment or thermal treatment (heat shock) at 95° C. Thus, a bead having bound thereto single-stranded oligonucleotides is produced.

In a conventional method, an oligonucleotide having a nucleic acid capture sequence exposed at the 3' end may be bound onto a bead using, as a template, a barcode linker having a nucleic acid capture sequence exposed at the 3' end without treatment with a restriction enzyme. In this case, primers for the nucleic acid amplification reaction in the step (i) are designed so as to anneal with the nucleic acid capture sequence. However, for example, when the nucleic acid capture sequence is an oligo(dT), the temperature for annealing of the primers becomes lower, resulting in an inappropriate nucleic acid amplification reaction. Therefore, it is necessary to arrange a primer complementary sequence at the 3' end of the nucleic acid capture sequence. When the primer complementary sequence of the oligonucleotide on the bead is bound to the 3' end and the nucleic acid capture sequence is not exposed at the 3' end, the nucleic acid capture sequence cannot capture a nucleic acid satisfactorily. Accordingly, it is necessary to expose the nucleic acid capture sequence at the 3' end of the oligonucleotide on the bead. In the present invention, it is necessary to arrange the restriction enzyme recognition sequence at a predetermined position to perform a treatment with a restriction enzyme.

In the present invention, the bead may have any size as long as the bead can be bound to an oligonucleotide capable of collecting a nucleic acid derived from a single cell, and the size is preferably from 20 μm to 40 μm. In addition, a short oligonucleotide may be added in advance to the bead. When an amplified product obtained using a barcode linker as a template is bound to the oligonucleotide added in advance to the bead, an oligonucleotide having a barcode sequence can be bound onto the bead. As the bead of the present invention, there may be given a bead for 454 sequencing included in a Roche emPCR kit.

In the present invention, the bead has a specific gravity higher than that of an aqueous solution, a buffer, or a solution containing a nucleic acid extraction reagent, and preferably has a specific gravity higher than 1. The bead of the present invention is preferably one that precipitates in an aqueous solution, a buffer, or a solution containing a nucleic acid extraction reagent when left to stand still for several minutes, or one that precipitates by centrifugation. In addition, when an avidin-bound magnetic material is used for collection of the bead after PCR, the bead is preferably made of a material having no reactivity with the magnetic material.

Examples of the bead used in the present invention may include: organic polymer beads, such as a resin bead formed of polystyrene or polypropylene; semiconductor beads including a quantum dot (semiconductor nanoparticle) formed of a semiconductor material, such as cadmium selenide (CdSe), zinc sulfide (ZnS), cadmium sulfide (CdS), zinc selenide (ZnSe), or zinc oxide (ZnO); a metallic bead formed of, for example, gold; and a polymer bead, such as a silica bead. In addition, examples of the bead in the present invention include beads formed of materials such as cellulose, a cellulose derivative, an acrylic resin, glass, silica gel, polystyrene, gelatin, polyvinylpyrrolidone, a copolymer of vinyl and acrylamide, and divinylbenzene-crosslinked polystyrene (see Merrifield Biochemistry 1964, 3, 1385-1390), polyacrylamide, a latex gel, polystyrene, dextran, a rubber, silicon, plastic, nitrocellulose, cellulose, natural sea sponge, silica gel, glass, metal plastic, cellulose, crosslinkeddextran (e.g., Sephadex™), and an agarose gel (Sepharose™). Agarose gel (Sepharose™) beads are preferred.

According to the present invention, when a nucleic acid amplification reaction is performed using one bead and one barcode linker molecule in a droplet, $4^n$ kinds of beads can be produced by one nucleic acid amplification reaction depending on the kind of the barcode sequence with the assumption that the number of bases of the barcode sequence is n. A plurality of oligonucleotide molecules each having one kind of barcode sequence are bound to each bead. That is, the barcode sequences in the oligonucleotides on the respective beads of the present invention are base sequences different from bead to bead.

The present invention also encompasses a bead for analyzing the composition of nucleic acids derived from a single cell obtained by the production method. The bead for analyzing the composition of nucleic acids derived from a single cell of the present invention may be supplied as a kit including two or more kinds (preferably 10 to $10^6$ kinds, more preferably $10^3$ to $10^5$ kinds) of beads. When oligonucleotides are added to the beads by emulsion PCR, beads each having a particular barcode sequence different from barcode sequences of the other beads can be prepared. According to the method of the present invention, the proportion of beads having barcode sequences identical to those of other beads can be suppressed to about 5% or less with respect to all beads used for the emulsion PCR. In addition, when the proportion of beads having barcode sequences identical to those of other beads is about 5%, it is less likely to add the same barcode sequence to different cells because an analysis method using the microplate of the present invention includes adjusting the number of cells inoculated.

The present invention further encompasses a microplate including a plurality of reaction wells, in which one bead obtained by the manufacture method is arranged in one reaction well, and barcode sequences are base sequences different from bead to bead. The microplate includes a plurality of reaction wells on a solid-phase substrate. The shape of the microplate is not particularly limited, and is, for example, a rectangle when illustrated in a plan view. The microplate of the present invention may be produced by a method of producing a microplate including the following steps.

(a) A step of preparing a microplate including a plurality of reaction wells.
(b) A step of adding a solution including beads onto the microplate, in which the ratio of the diameter of each reaction well to the diameter of each bead is from about 1.2 to about 1.75. In this step, the ratio of the depth of each reaction well to the diameter of each bead is preferably from about 1.5 to about 2.5. Specifically, the diameter of the reaction well is preferably from 24 μm to 70 μm. When the diameter of the bead is 20 μm, the diameter of the reaction well is from 24 μm to 35 μm. In addition, the depth of the reaction well is preferably from 30 μm to 100 μm. When the diameter of the bead is 20 μm, the depth of the reaction well is from 30 μm to 50 μm (preferably from 30 μm to 40 μm).
(c) A step of arranging one bead in one reaction well by covering the microplate with a semipermeable membrane and squeezing the surface of the microplate with a pressing member.

The shape of the microplate is not particularly limited, and is, for example, a rectangle when illustrated in a plan view. The reaction well may have a general cylindrical shape or may be U-shaped, V-shaped, or hemispherical in cross-section. In addition, the reaction well may have a size enough to place one bead and one cell in the well. When the reaction well has a cylindrical shape, the reaction well has a diameter of about 25 μm, a depth of about 40 μm, and a volume of about 20 pl. When the reaction well has a smaller volume, the rate of nucleic acids collected can be raised because the number of the nucleic acids adsorbed in a non-specific manner to the surface of the reaction well decreases.

The microplate is required to be made of a material that can prevent a substance from being substantially exchanged between the inside and the outside of the reaction well. The material of the microplate is preferably an elastic polymer resin because the resin can be easily molded, is inexpensive, and facilitates collection of beads. For example, polydimethylsiloxane (PDMS), polymethyl methacrylate (PMMA) (acrylic resin), polycarbonate (PC), polystyrene (PS), polypropylene (PP), polyethylene (PE), and polyethylene terephthalate (PET) are given as examples, and in particular, polydimethylsiloxane (hereinafter abbreviated as "PDMS") is preferred. In addition, the number of the reaction wells on the microplate may be appropriately set depending on the size of the slide, and is preferably 100,000 or more.

In the step (a), the microplate including a plurality of reaction wells may be produced by any method, or may be a commercially available product. For example, the microplate may be manufactured by: preparing a matrix of the microplate; pouring, for example, a thermosetting resin to the matrix; and curing and molding the thermosetting resin by heating using a heater or the like under reduced pressure. Alternatively, a photocurable resin may be used instead of the thermosetting resin. The photocurable resin is cured by molding the resin by irradiation with light, such as ultraviolet light. Alternatively, the microplate may also be manufactured by injection molding of a thermoplastic resin under reduced pressure using a matrix having a draft angle and a mold release agent. In addition, the reaction wells may be formed on a solid-phase substrate by a method such as nanoimprint or cutting work.

The inner surface of each reaction well is preferably subjected to hydrophilic treatment. The hydrophilic treatment may be performed by a method such as application of a hydrophilic resin, surface treatment based on a photocatalyst effect, coating treatment with an inorganic substance, such as an alkali silicate, etching treatment, or plasma cluster treatment. The microplate of the present invention is preferably subjected to a hydrophilic treatment method by plasma cluster treatment to exposure the microplate to plasma.

The step (b) is a step of adding beads onto the microplate prepared in the step (a) to arrange the beads in reaction wells. The beads may be suspended in a solution and then added onto the microplate. In order to arrange one bead in one reaction well, the ratio of the diameter of the reaction well to the diameter of the bead is preferably from about 1.2 to about 1.75. In addition, the ratio of the depth of the reaction well to the diameter of the bead is preferably from about 1.5 to about 2.5. When the ratio between the diameter or depth of the reaction well and the diameter of the bead falls within the above-mentioned range, one bead can be arranged in one reaction well even in the case where the beads are added to the microplate in an excessive amount relative to the number of the reaction wells. When the ratio of the diameter of the reaction well to the diameter of the bead is about 1.75 or less, the second bead is placed on the first bead in the reaction well including the first bead already arranged therein, and can be removed by the following step (c) using a pressing member. In addition, when the ratio of the diameter of the reaction well to the diameter of the bead is about 1.2 or more, one bead and one cell can be placed in the reaction well. In addition, the case where the ratio of the depth of the reaction well to the diameter of the bead is about 1.5 or more is preferred because contamination caused in capture of nucleic acids in one cell by one bead can be prevented. When the ratio of the depth of the reaction well to the diameter of the bead is about 2.5 or less, the second bead can be removed by the following step (c) using a pressing member because the microplate is elastic. When the ratio between the diameter or depth of the reaction well and the diameter of the bead is beyond the above-mentioned range, it is necessary to add beads in a small amount relative to the number of the reaction wells to arrange one bead in one reaction well, resulting in a reaction well including no bead. Accordingly, the number of cells capable of capturing nucleic acids decreases, and an efficient analysis cannot be performed. The beads are required to be added onto the microplate at a density enough to place the beads in at least all of the reaction wells according to Poisson distribution. For example, the number of the beads to be added is preferably about 1.1 times to about 1.3 times as large as that of the reaction wells on the microplate.

In the step (c), the whole of the microplate onto which the beads have been added in the step (b) is covered with a semipermeable membrane, and the surface of the microplate is squeezed with a pressing member to arrange one bead in one reaction well. The term "squeeze" refers to moving the pressing member on the semipermeable membrane along the surface of the microplate while applying a pressure from above the member. The ratio between the diameter or depth of the reaction well and the diameter of the bead has been adjusted, and hence when the pressing member is moved (slid) on the semipermeable membrane, each bead is placed in a reaction well including no bead, or excessive beads are removed from the reaction well already including the bead without the placement of another bead. The pressing member only needs to be one that can apply an appropriate pressure and can squeeze the surface (scrub the surface compressively) from above the semipermeable membrane. The pressing member only needs to be a rod-like member having a certain length, and the cross section of the pressing member may have any shape, such as a circle, a triangle, or a square. Specific examples of the pressing member may include a roller having a rotatable surface and a rod-like or plate-like member, such as a scale. According to the step (c), a microplate having one bead arranged in each of substantially all reaction wells can be produced. The semipermeable membrane may be, for example, a dialysis membrane known per se. The phrase "in each of substantially all reaction wells" means that the beads are arranged in at least 80% or more, preferably 90% or more, more preferably 95% or more, particularly preferably 98% or more of the reaction wells with respect to all the reaction wells of the microplate.

In addition, the present invention also encompasses a method of analyzing a composition of nucleic acids derived from a single cell using the above-mentioned beads or microplate having beads arranged in reaction wells. The nucleic acids of the present invention may be DNAs or RNAs. The beads manufactured in the present invention can collect total RNA obtained from one eukaryotic cell or almost the same amount of total RNA as that of the total RNA obtained from one eukaryotic cell. One cell is known to contain about 10 pg of total RNA and $3 \times 10^5$ to $5 \times 10^5$ mRNA molecules, though the values vary depending on the kind of the cell. The bead produced in the present invention has bound thereto $10^6$ to $8 \times 10^6$ oligonucleotide molecules, and hence is considered to be able to collect the total of mRNAs contained in one cell. When the number of oligonucleotide molecules bound onto the bead is smaller than $10^6$, the bead cannot collect the total of mRNAs contained in one cell, while the number of oligonucleotide molecules bound onto the bead is larger than $8 \times 10^6$, a reaction for amplifying nucleic acids captured may be inhibited.

The method of analyzing a composition of nucleic acids derived from a single cell includes the following steps (1) to (3):

(1) a step of extracting nucleic acids from a cell under a state in which one bead obtained by the production method of the present invention is brought into contact with one cell to bind the nucleic acids derived from the cell to oligonucleotides on the bead;

(2) a step of performing a nucleic acid amplification reaction using, as templates, the nucleic acids bound to the oligonucleotides on the bead; and (3) a step of determining barcode sequences in resultant amplified fragments to analyze the composition of nucleic acids derived from a single cell with the assumption that fragments having the same barcode sequence are defined as those derived from the same cell.

In the step (1), one bead is brought into contact with one cell. The term "contact" as used herein does not mean that the bead is physically and directly in contact with the cell, and means that one bead and one cell are present as a single unit in a closed area that is not in contact with another cell or another bead, and means a state in which nucleic acids extracted from a cell can be bound to oligonucleotides on a bead in a single unit. For example, one bead and one cell may be present as a single unit in a single container, in a single aqueous phase of an emulsion, in a single compartment, such as a reaction well of a microplate (micro titer plate), or in a single liquid droplet in a micro flow path. In this description, the microplate is used synonymously with the micro titer plate. Any means for acquiring one cell may be adopted, and there may be given, for example, means for separating a tissue obtained from a living body by enzymatic treatment, means for collecting one cell using a cell sorter, and means for acquiring one cell using a microfluid. One cell is preferably acquired by bringing one bead into contact with one cell on a reaction well of a microplate to capture nucleic acids derived from the cell by oligonucleotides on the bead.

Known means may be employed as means for extracting a nucleic acid from a cell. For example, a nucleic acid extraction reagent (for example, a surfactant, such as lithium dodecyl sulfate or Nonidet P-40) may be added to a compartment (such as a tube or a well of a microplate) including one cell to separate nucleic acids from the cell. When the nucleic acids separated from the cell are brought into contact with a bead, the nucleic acids are bound to nucleic acid capture sequences of oligonucleotides on the bead. When the beads having bound thereto the nucleic acids are collected, a nucleic acid of interest can be collected. After collection of the beads, unnecessary cell components and the like may be removed by washing.

In the analysis method of the present invention, a microplate having one bead arranged in one reaction well is preferably used. In this case, when cells are inoculated into the microplate in which one bead has been arranged in one reaction well in advance to arrange one cell in one reaction well, one bead is in contact with one cell. In order to bring one bead into contact with one cell, it is necessary to add cells to the microplate according to Poisson distribution. In order to prevent two cells from being placed in one reaction well as much as possible, for example, cells are added thereto after the number of the cells is adjusted to 1/10 or less of the number of the reaction wells on the microplate. In this case, one cell can be placed in one reaction well with a probability of about 95%. Further, cells are preferably added thereto after the number of the cells is adjusted to 1/30 or less of the number of the reaction wells on the microplate. In this case, one cell can be placed in one reaction well with a probability of about 98%. In the case where cells are inoculated on a microplate in which no beads have been arranged in reaction wells in advance, and then beads are inoculated thereinto, it is necessary to inoculate both the cells and the beads in small amounts, and hence the number of cells capable of actually capturing nucleic acids is reduced. In the microplate of the present invention, one bead is arranged in each of 80% to 98% of the reaction wells, and hence nucleic acids can be captured completely from many cells because one cell is arranged in one reaction well.

After addition of cells to the microplate, the microplate is preferably covered with a semipermeable membrane. The membrane can prevent the inside of each reaction well from being in contact with another reaction well, and can place one bead and one cell as a single unit in a closed area that is not in contact with another cell and another bead. A nucleic acid extraction reagent capable of solubilizing cells to extract nucleic acids may be added from above the semipermeable membrane. The nucleic acid extraction reagent is passed through the semipermeable membrane, arrives at the inside of each reaction well, and dissolves the cell to extract nucleic acids. The nucleic acids derived from each cell are captured by oligonucleotides on the bead present in the same reaction well. When the beads having bound thereto the nucleic acids are collected in one container, nucleic acids of interest can be collected. After collection of the beads, unnecessary cell components and the like may be removed by washing. The nucleic acid extraction reagent preferably contains a surfactant.

According to the step (1), a microplate including reaction wells that include beads including nucleic acids captured can be prepared. The microplate having beads arranged therein preferably has a portable size. The microplate may be conveyed after capture of nucleic acids from cells to perform, in another place, a nucleic acid amplification reaction and an analysis of barcode sequences or the like. When the nucleic acids are mRNAs, after the performance of only a reverse transcription reaction, the microplate or beads collected from the microplate may be conveyed.

After that, in the step (2), a nucleic acid amplification reaction is performed for the nucleic acids bound to oligonucleotides on the beads. When the nucleic acids of interest are mRNAs, a reverse transcription reaction may be performed before the nucleic acid amplification reaction. First, a plurality of beads that are present separately in a single area, such as a reaction well of a microplate, may be collected, and then subjected to the reverse transcription reaction and the nucleic acid amplification reaction at one time. Hundreds to tens of thousands of beads collected from the microplate may be subjected to the reactions simultaneously. The beads may be collected from the microplate by turning the microplate upside down so that the reaction wells of the microplate may face down and dropping the beads into a container placed under the microplate. The microplate is made of an elastic material, and hence the beads can be easily dropped from the reaction wells by shaking the microplate a plurality of times or by inflecting the microplate. Alternatively, the beads may be separately subjected to the reverse transcription reaction and the nucleic acid amplification reaction by emulsion PCR without the collection of a plurality of beads. Primers to be used may be any primers, but are preferably primers capable of amplifying any nucleic acids. Amplified products obtained are those each obtained by adding a barcode sequence to a nucleic acid derived from a single cell. When a plurality of beads (having barcode sequences different from bead to bead) are collected and subjected to the nucleic acid amplification reaction, different barcode sequences may be separately added to a plurality of cells.

In the step (3), the barcode sequences of the resultant amplified fragments are determined, and fragments having the same barcode sequence are identified as fragments derived from the same cell to analyze the composition of the nucleic acids derived from a single cell. When the barcode sequence included in each amplified fragment is determined to specify a cell from which the amplified fragment is derived, the cells can be classified. When the resultant amplified products are analyzed using a sequencer, a nucleic acid amplification reaction may be performed to add a linker or the like suitable for the sequencer to be used. According to the present invention, the barcode sequence is added to the 3' end of a nucleic acid of interest. The barcode sequence is determined by an analysis using preferably a sequencer, particularly preferably a next-generation sequencer. Examples of the next-generation DNA sequencer include, but not limited to, devices such as GS FLX manufactured by Roche, SOLID manufactured by Life Technologies, sequencer series such as GAIIx and HiSeq manufactured by Illumina, PacBio RS II system manufactured by Pacific Biosciences, and Ion PGM manufactured by Life Technologies.

In the present invention, in order to determine a barcode, and in order to acquire expression information derived from as many cells as possible, only the sequence of the 3' end of a gene derived from a cell is preferably determined. Gene expression analyses using a next-generation sequencer are divided into an analysis called mRNA-seq and a tag (partial gene) analysis. The mRNA-seq is performed, in many cases, by a method involving fragmenting mRNA isolated, subjecting the resultant fragments to reverse transcription to form a double strand, and adding an adaptor sequence thereto. Alternatively, there is known strand-specific RNA-seq, which involves binding an oligo-RNA having an adaptor sequence to fragmented mRNA and then performing reverse transcription to form a double strand. In addition, a method for exhaustive gene quantification using a sequencer based on a Sanger method, called SAGE, has been developed (U.S. Pat. No. 6,746,845 (B2)). In such quantification method, a gene tag is ligated to form a concatemer, and the method is suitably used as the analysis method of the present invention (Asmann Y W, Klee E W, Thompson E A, Perez E A, Middha S, Oberg A L, Therneau T M, Smith D I, Poland G A, Wieben E D, Kocher J P. BMCGenomics. 2009 Nov. 16; 10:531; MorrissyAS, Morin R D, Delaney A, ZengT, McDonald H, Jones S, Zhao Y, Hirst M, Marra M A. Genome Res. 2009 October; 19(10): 1825-35. Epub 2009 Jun. 18). A method for exhaustive gene quantification starting from a start point of transcription developed by the inventors of the present invention, called 5' SAGE, may also be adopted (Hashimoto, S., Suzuki, Y., Kasai, Y., Morohoshi, k., Yamada, T., Sese, J., Morishita, S., Sugano, S., and Matsushima, K. Nature Biotechnol., 22, 1146-1149 (2004); Japanese Patent No. 3,845,416, Hashimoto, S., Qu, W., Ahsan, B., Ogoshi, K., Sasaki, A., Nakatani, Y., Lee, Y., Ogawa, M., Ametani, A., Suzuki, Y., Sugano, S., Lee, C. C., Nutter, R. C., Morishita, S., and Matsushima, K. PLoS One, 4, e4108 (2009)).

When the barcode sequences are determined, nucleic acids derived from the respective cells can be distinguished to analyze and compare the compositions of the nucleic acids derived from the respective cells. Specifically, a sequence obtained by cutting an adaptor sequence off from a base sequence determined by a sequencer is defined as a sequence of a gene fragment, and the sequence of the gene fragment derived from a single cell is separated on the basis of the barcode sequence using a computer, followed by determination of a gene name and an expression level of the gene from database on the basis of the sequence of the gene fragment. A list of the compositions of nucleic acids derived from a single cell, which shows names and expression levels of the genes, can be made.

The present invention further encompasses a reagent kit for use in the analysis method, which includes the microplate of the present invention and a nucleic acid extraction reagent for dissolving a cell. The reagent kit may further include a semipermeable membrane, a buffer, a reagent necessary for a reverse transcription reaction, other necessary reagents, an instruction leaflet, and the like.

EXAMPLES

The present invention is hereinafter more specifically described by way of the following Examples. However, the present invention is not limited to Examples.

(Example 1) Production of Bead for Analyzing Composition of Nucleic Acids Derived from Single Cell A bead for analyzing the composition of nucleic acids derived from a single cell was produced in accordance with the following method (FIG. 1A).

Emulsion PCR was performed using a barcode linker. The barcode linker has a sequence represented by SEQ ID NO: 2 below, and the sequence includes a poly(dA) sequence (sequence complementary to an oligo(dT) sequence) and primer complementary sequences for PCR amplification. The barcode linker was synthesized by Integrated DNA Technologies.

```
Barcode linker (SEQ ID NO: 2):
5'-CCATCTCATCCCTGCGTGTCTCCGACTCAGGCAGTGAAAAAAAAA

AAAAAAAAAAANNNNNNNNNNNNNCTGAGACTGCCAAGGCACACAGGGG

ATAGG-3'
N = A or T or C or G
```

Purification Procedure: PAGE Purification

The emulsion PCR was performed using a Roche emPCR kit. Beads for 454 sequencing included in the Roche emPCR kit support thereon millions of oligonucleotide molecules each having a specific sequence, and each of the beads has a size of 20 μm.

The PCR was performed using primers having sequences of

```
                                        (SEQ ID NO: 3)
    5'-CCTATCCCCTGTGTGCCTTGGCAGTCT
and
                                        (SEQ ID NO: 4)
    5'-CCATCTCATCCCTGCGTGTCTCCGA
``` by incubating a sample at 94° C. for 4 minutes and then repeating, 50 times, a cycle of 94° C. for 30 seconds, 58° C. for 4.5 minutes, and 68° C. for 30 seconds, followed by maintaining the resultant at 10° C. PCR-amplified products bound to oligonucleotides on the beads for 454 sequencing were produced.

After that, the beads having been subjected to the emulsion PCR were purified in accordance with a manual of the Roche emPCR kit. First, each of the oligonucleotides on the bead was denatured into a single strand by alkali treatment, and an enrichment primer (a primer that recognizes, and is bound to, the 3' end of a barcode linker, and is not bound thereto when a sequence for amplification of the barcode linker is not present on the bead) included in the Roche emPCR kit was bound to the single-stranded oligonucleotide on the bead, followed by purification of the beads using streptavidin magnet beads. After that, 20 μl of 10×NEB buffer 2, 10 μl of exo-klenow (New England Biolabs), 20 μl of dNTP mix (2.5 mM), and 150 μl of $H_2O$ were added to the purified beads, and the resultant was allowed to react at 37° C. for 1 hour and at 70° C. for 10 minutes to elongate the enrichment primer (in order to purify the beads having been subjected to the emulsion PCR, the enrichment primer is partially bound and has a double-stranded structure) to a restriction enzyme site, thereby synthesizing a double strand. This is because cleavage with BtsI cannot be performed for a single-stranded oligonucleotide.

The double-stranded DNAs amplified on the beads were treated with a restriction enzyme BtsI (55° C., 3 hours) so that an oligo(dT) sequence was arranged at the 3' end of each of the double-stranded DNAs on the beads.

After the treatment with the restriction enzyme, the oligonucleotides were subjected to alkali treatment with 0.125 N NaOH and then to heat-shock treatment at 95° C. to denature the double-stranded DNAs on the beads into single-stranded DNAs, and the beads were washed with Low TE (10 mM Tris-HCl pH 8.0, 0.1 mM EDTA) by centrifugation. Millions of oligonucleotide molecules each including a single-stranded DNA are considered to be bound onto the surface of each bead.

FIG. 2 is a figure for showing results of sequencing for oligo sequences on 17 beads selected randomly, the sequencing being performed using a 3730 capillary sequencer (Applied Biosystems) by emulsion PCR using barcode linkers. The results reveal that the 17 beads have different barcode sequences.

(Example 2) Analysis of Gene Expression in Peripheral Blood Mononuclear Cells Using Beads of the Present Invention Gene expression in peripheral blood mononuclear cells was analyzed using the beads produced in Example 1 by the following method (FIG. 1B).

A polydimethylsiloxane microplate (hereinafter also referred to as "PDMS slide") including $1.7 \times 10^5$ to $2.3 \times 10^5$ wells each having a diameter of from 35 μm to 40 μm and a depth of 50 μm was subjected to plasma cluster treatment ($O_2$ 10000, 75 W, 10 sec) to forma hydrophilic surface. The PDMS slide having been subjected to the plasma cluster treatment was treated with 1% BSA for 30 minutes, washed with distilled water, and then washed with PBS.

The beads produced in Example 1 were placed on the PDMS slide after the number of the beads was adjusted to ¼ or less of the number of the wells of PDMS. In the same manner as above, the cells were also placed on the slide after the number of the cells was adjusted to ¼ or less of the number of the wells of PDMS. This is intended to prevent two or more beads or cells from being placed in one well.

The slide was left to stand for from 10 minutes to 15 minutes, and was then washed with PBS and covered with a dialysis membrane (12,000 to 14,000 MWCO regenerated cellulose dialysis tube, 25-mm flat width, Fisher Scientific).

A liquid that remained between the dialysis membrane and the slide was aspirated from the side using PIPETMAN so that the liquid was prevented from remaining between the dialysis membrane and the slide as much as possible.

300 μl of Lysis buffer (500 mM LiCl in 100 mM TRIS buffer (pH 7.5) with 1% lithium dodecyl sulfate, 10 mM EDTA, and 5 mM DTT) was added from above the dialysis membrane.

The slide was left to stand at room temperature for 20 minutes and then at 4° C. for 10 minutes.

After that, the dialysis membrane was peeled off, and the PDMS slide was turned upside down and immersed in a petri dish including 2 ml of cold Lysis buffer to drop the cells in the Lysis buffer.

The resultant was centrifuged at 10,000 rpm for 10 seconds to collect the beads. Subsequently, the beads were suspended in buffer A (100 mM Tris, pH 7.5, 500 mM LiCl, 1 mM EDTA, 4° C.), followed by further centrifugation at 10,000 rpm for 10 seconds to collect the beads. Subsequently, the beads collected were suspended in buffer B (20 mM Tris, pH 7.5, 50 mM KCl, 3 mM MgCl), and the suspension was centrifuged at 10,000 rpm.

The beads in a pellet state were used to synthesize 1st strand cDNA by performing a reverse transcription reaction for mRNAs bound to each bead.

The reverse transcription reaction was performed using 5× First strand buffer, DTT, dNTP mix, SMARTer IIA Oligonucleotide (12 uM), an RNase inhibitor, and Smartscribe reverse transcriptase (100 units) by incubating a sample at 42° C. for 1 hour and at 70° C. for 10 minutes.

Next, PCR was performed to synthesize 2nd strand. The PCR was performed using 10 μl of a sample, 50 μl of 5× buffer, 4 μl of Bio-F primer (12 μM) (5'-Bio-TEG-CCTATC-CCCTGTGTGCCTTGGCAGTCT-3 (SEQ ID NO: 5)), 4 μl of 5' PCR primer IIA (12 μM), 34 μl of H$_2$O, and 2 μl of DNA polymerase Ver. 2 Might Amp by repeating, 20 times, a cycle of 98° C. for 2 minutes, 98° C. for 10 seconds, 60° C. for 15 seconds, and 68° C. for 4 minutes.

Next, sequences of PCR products were determined.

After PCR, the PCR products were purified with 100 μl of AMpure. Further, the PCR products were subjected to agarose electrophoresis in accordance with a conventional method to purify amplified products each having a size of 500 bp or more. The products were sonicated to cleave the DNAs into fragments each having a size of from 300 bp to 500 bp suited for a next-generation sequencer. In addition, the amplified products were blunt-ended using End-It™ DNA End-Repair Kit (AR BROWN). The amplified products were further purified and concentrated using MinElute PCR Purification Kit (Qiagen) to prepare elute DNAs.

Next, in order to bind an adaptor having an oligo-binding sequence of the next-generation sequencer, adaptor PCR was performed to construct a library for next-generation sequencing. Specifically, 34 μl of the elute DNAs, 5 μl of Buffer×10, 5 μl of ATP, 5 μl of dNTP, and 5 μl of an enzyme were mixed to prepare a solution, and the solution was left to stand at room temperature for 40 minutes, and a double-stranded linker including Solexa 3 adaptor-1 and Solexa 3 adaptor-2 for Hiseq below was added to DNAs having been blunt-ended with T4 DNA ligase.

```
Solexa 3 adaptor-1:
                                        (SEQ ID NO: 6)
5'-GTGACTGGAGTTCAGACGTGTGCTCTTCCGATCT Solexa 3 adaptor-2:
                                        (SEQ ID NO: 7)
5'-/5Phos/AGATCGGAAGAGCACACGTCTGAACTCCAGTCAC/
3AmMC7/-3'
```

After that, 2 μl of 10 × EXTaq buffer, 1.6 μl of dNTP (2.5 mM), 2 μl of 454 Solexa primer (10 μM)

```
                                        (SEQ ID NO: 8)
5-AATGATACGGCGACCACCGAGATCTACACTCTTTCCCTACACGACG
CTCTTCCGATCTCCTATCCCCTGTGTGCCTTGGCAGTCT-3,
```

2 μl of Index 1 primer (10 μM)

```
                                        (SEQ ID NO: 9)
5-CAAGCAGAAGACGGCATACGAGATCGTGATGTGACTGGAGTTC,
```

9.2 μl of H$_2$O, and 0.5 μl of EX Taq HS (5 μ/μl) were mixed, and the mixture was subjected to PCR for a region including a barcode and the 3' end of the gene. The PCR was performed by incubating a sample at 95° C. for 3 minutes and then repeating, 20 times, a cycle of 95° C. for 20 seconds, 57° C. for 30 seconds, and 72° C. for 30 seconds. After that, the amplified products were left to stand still on ice. The PCR amplified products were subjected to gel electrophoresis, and bands were cut to collect cDNAs.

The cDNAs collected were purified and concentrated using MinElute PCR Purification Kit (Qiagen). The sequences were analyzed using HiSeq 2500 (Illumina, Inc.).

FIG. 3 is a figure for showing an example of results of sequencing of the mRNAs collected from PBMCs using the beads of the present invention. The results reveal that a barcode sequence was added to the 3' end of Homo sapiens nucleophosmin.

(Example 3) Production of Beads and Microplate for Analyzing Composition of Nucleic Acids Derived from Single Cell Beads for analyzing the composition of nucleic acids derived from a single cell were produced by a method obtained by modifying the method of Example 1.

First, emulsion PCR was performed using a barcode linker. The barcode linker used has the following sequence represented by SEQ ID NO: 31. The barcode linker has, in addition to primer complementary sequences for the emulsion PCR, any base sequence for preventing non-specific amplification inserted at the upstream of the barcode sequence (the underlined part on the 3' side of the barcode sequence). The any base sequence may be used to synthesize a 2nd strand after reverse transcription for the mRNAs captured. The underlined part on the 5' side of the poly(dA) sequence is a restriction enzyme site. The barcode linker was synthesized by Integrated DNA Technologies.

```
Barcode linker (SEQ ID NO: 31):
5'-CCATCTCATCCCTGCGTGTCTCCGACTCAGGCAGTGAAAAAAAAA

AAAAAAAAAAAAAAAAANNNNNNNNNNNNNNACATAGGCCGTCTTCAGCCG

CTGAGACTGCCAAGGCACACAGGGGATAGG-3'
N = A or T or C or G
```

Purification Procedure: PAGE Purification

The emulsion PCR was performed using a Roche emPCR kit by a method obtained by modifying the method of Example 1. Beads for 454 sequencing included in the Roche emPCR kit support thereon millions of oligonucleotide molecules each having a specific sequence, and each of the beads has a size of 20 μm.

The PCR was performed using a primer including biotin added on the 5' side:

```
                                        (SEQ ID NO: 32)
    5'-/5Biosg//iSp18/CGTATCGCCTCCCTCGCGCCAT-3'
    and
                                        (SEQ ID NO: 33)
    5'-CCTATCCCCTGTGTGCCTTGGCAGTCT-3'.
```

After that, only beads on which amplification by PCR was performed were selected and collected. The beads on which amplification by PCR was performed were bound to biotin at the 5' end of each amplified product, and hence the beads were purified using avidin-bound magnetic beads. In this example, the beads were able to be purified without using an enrichment primer after the alkali treatment like Example 1.

Next, the double-stranded DNAs amplified on the beads were treated with a restriction enzyme BtsI (55° C., 3 hours) so that an oligo(dT) sequence was arranged at the 3' end of each of the double-stranded DNAs on the beads.

After the treatment with the restriction enzyme, the oligonucleotides were subjected to alkali treatment with 0.125 N NaOH and then to heat-shock treatment at 95° C. to denature the double-stranded DNAs on the beads into single-stranded DNAs, and the beads were washed with Low TE (10 mM Tris-HCl pH 8.0, 0.1 mM EDTA) by centrifugation. Millions of oligonucleotide molecules each including a single-stranded DNA are considered to be bound onto the surface of each bead.

Next, the beads were arranged in reaction wells of a microplate. A microplate (PDMS slide) including $2.0 \times 10^5$ wells each having a diameter of 25 μm and a depth of 40 μm was subjected to plasma cluster treatment, treated with 1% BSA for 30 minutes, washed with distilled water, and then washed with PBS.

The resultant beads (diameter: 20 μm) were placed on the PDMS slide after the number of the beads was adjusted to from about 1.1 times to about 1.3 times of 200,000. The slide was covered with a dialysis membrane (12,000 to 14,000 MWCO regenerated cellulose dialysis tube, 25-mm flat width, Fisher Scientific), and the membrane was squeezed from above with a roller or a scale to push the beads out from the wells including two beads so that one bead was arranged in one well. The slide after the squeezing is shown in FIG. 9.

(Example 4) Analysis of Gene Expression of Peripheral Blood Mononuclear Cells Using Beads of the Present Invention The microplate (PDMS slide) produced in Example 3, in which the beads were arranged in reaction wells, was used to analyze gene expression of peripheral blood mononuclear cells by a method obtained by modifying the method of Example 2.

The cells were placed on the slide after the number of the cells was adjusted to 1/20 or less of the number of the wells of the PDMS slide produced in Example 3. The slide was left to stand for from 10 minutes to 15 minutes, and was then washed with PBS and covered with a dialysis membrane, and 300 μl of Lysis buffer (500 mM LiCl in 100 mM TRIS buffer (pH 7.5) with 1% lithium dodecyl sulfate, 10 mM EDTA, and 5 mM DTT) was added from above the dialysis membrane.

The slide was left to stand at room temperature for 20 minutes and then at 4° C. for 10 minutes.

After that, the dialysis membrane was peeled off, and the PDMS slide was turned upside down and immersed in a petri dish including 2 ml of cold Lysis buffer to drop the cells in the Lysis buffer, followed by centrifugation to collect the beads.

The beads in a pellet state were used to synthesize 1st strand cDNA by performing a reverse transcription reaction for mRNAs bound to each bead.

Next, PCR was performed to synthesize 2nd strand. The PCR was performed using 10 μl of a sample, 50 μl of 5× buffer, 4 μl of a forward primer (12 μM) (5'-/5BioTEG/GCGGCTGAAGACGGCCTATGT-3 (SEQ ID NO: 34)), 4 μl of 5' PCR primer IIA (12 μM), 34 μl of $H_2O$, and 2 μl of DNA polymerase Ver. 2 Might Amp by repeating, 20 times, a cycle of 98° C. for 2 minutes, 98° C. for 10 seconds, 60° C. for 15 seconds, and 68° C. for 4 minutes.

Next, sequences of the PCR products were determined. The PCR products were purified, and a library for next-generation sequencing was constructed in accordance with a conventional method to analyze the sequences using HiSeq 2500 (Illumina, Inc.).

FIG. 4 is a table for showing an example of results of the sequences of the mRNAs collected using the beads of the present invention from the peripheral blood mononuclear cells. COX4I1 gene and TRAPPC5 gene shown in the left column of FIG. 4 had the same barcode sequence added, and hence were found to be derived from the same cell. Meanwhile, COX4TI gene, MIF gene, and RPS18 gene shown in the right column had different barcode sequences added, and hence it was revealed that the same gene was expressed in a plurality of different cells.

(Example 5) Analysis of Gene Expression of Hepatocellular Carcinoma Cell Line Using Beads of the Present Invention In the same way as in Example 4, gene expression of a hepatocellular carcinoma cell line (hepatocellular carcinoma cancer stem like cell (HBV+)) was analyzed. The hepatocellular carcinoma cell line used was obtained from a patient with hepatitis B-positive hepatocellular carcinoma.

A sequence analysis by paired-end sequencing revealed that the number of reads that were able to detect genes and recognize barcodes was 919,239,370. FIG. 5 is a table for showing a part of results of barcode sequences capable of identifying cells, the numbers of genes, and the total numbers of reads.

FIG. 6 is a table for showing genes expressed in cells and identified with barcodes. Specific names of genes confirmed to be expressed in cells identified with barcode sequences and the numbers of reads are shown. The numbers of reads represent relative expression levels. It was found that the expression levels of the genes varied depending on the kinds of the cells, and it was able to be confirmed that the method of the present invention was able to analyze the gene expression in each cell.

FIG. 7 is a graph for showing a correlation between the numbers of reads of sequences and the numbers of genes observed. The number of reads per cell varies depending on the kind of the sequence used, and when the number of reads per cell is large, about 11,000 kinds of genes can be identified.

FIG. 8 is a graph for showing correlations between two cells. Two cells were randomly selected, and the gene frequencies per cell were compared. The highest correlation ($R^2$) between different cells was as high as 0.96. In addition, when a correlation was calculated from data of 50 Thy1-positive cells and 50 Thy1-negative cells, $R^2$ was as high as 0.993, i.e., a correlation was extremely high. The results reveal that errors of gene expression frequencies per cell are extremely small. In addition, as compared to another single cell gene analysis method (Smart-seq) (Ramskold D et al.: Nat Biotechnol (2012)), extremely high correlations were achieved in the analysis method of the present invention.

INDUSTRIAL APPLICABILITY

When the present invention is used, hundreds to tens of thousands of single cells can be simultaneously analyzed, and hence the present invention is expected to reveal configurationality of cell populations to enable one to grasp a true cell state, and to help clinical research in the future. Cells are greatly affected by a microenvironment, respond differently by a small number of molecules involved in transcription and translation, and produce probabilistic responses to some extent, and hence expression responses of different cells are considered to be different from each other.

For example, when transcriptomes of stem cells and differentiated cells can be individually clarified by the method according to the present invention, a process of differentiation can be observed with time, and the observation is useful for efficient formation of tissues and organs, and quality control of tissues and organs produced. In addition, when an analysis of expression according to the present invention is used to analyze properties or time-dependent changes of cancer subpopulations or to analyze, for example, an early cancer, a circulating cancer, or a cancer spread to another part, a stage of cancer progression can be observed. Further, a microenvironment (vascular endothelium, epithelium, fibroblast, or the like) around a cancer, which is important to keep the cancer, can also be observed. When gene expressions in axons and dendrites are individually clarified by the present invention to analyze functions of neurons, the present invention is considered to identify a cause of a neurological disease or to help development of a therapeutic agent.

The invention claimed is:

1. A microplate for use in a method of analyzing a composition of nucleic acids derived from a single cell, the microplate comprising a plurality of reaction wells and a plurality of beads,
the microplate having one bead arranged in each of 80% or more of the reaction wells,
each bead having bound thereto a plurality of molecules of single-stranded oligonucleotides,
the single-stranded oligonucleotides each having a nucleic acid capture sequence exposed at a 3' end and a barcode sequence on a 5' side of the nucleic acid capture sequence,
the barcode sequence comprising a base sequence that differs from bead to bead,
the beads satisfying a ratio of the diameter of each reaction well to the diameter of each bead of from 1.2 to 1.75,
the beads satisfying a ratio of a depth of each reaction well to the diameter of each bead of from about 1.5 to about 2.5.

2. The microplate according to claim 1, wherein the bead has a size of from 20 μm to 40 μm.

3. The microplate according to claim 1, which does not yet contain cells.

4. A method of producing the microplate of claim 1, the method comprising the following steps:
(a) preparing a microplate including a plurality of reaction wells;
(b) adding, onto the microplate, beads that satisfy a ratio of a diameter of each reaction well to a diameter of each bead of from 1.2 to 1.75 and a ratio of a depth of each reaction well to the diameter of each bead of from about 1.5 to about 2.5, each bead having bound thereto a plurality of molecules of single-stranded oligonucleotides, the single-stranded oligonucleotides each having a nucleic acid capture sequence exposed at a 3' end and a barcode sequence on a 5' side of the nucleic acid capture sequence, the barcode sequence comprising a base sequence that differs from bead to bead;
(c) arranging one bead in one reaction well by covering the microplate with a semipermeable membrane and squeezing a surface of the microplate with a pressing member.

5. A reagent kit for use in a method of analyzing a composition of nucleic acids derived from a single cell, the reagent kit comprising the microplate of claim 1 and a nucleic acid extraction reagent.

6. A method of analyzing a composition of nucleic acids derived from a single cell using the microplate of claim 1, the method comprising the following steps:
(1) capturing, after inoculating cells onto the microplate to arrange cells in the reaction wells in a manner where one bead and one cell are present as a single unit in each reaction well, and extracting nucleic acids from the cells in the reaction wells of the microplate, the nucleic acids derived from the cells by single-stranded oligonucleotides on each bead;
(2) performing a nucleic acid amplification reaction using, as templates, the nucleic acids captured by the single-stranded oligonucleotides on each bead to produce amplified fragments; and
(3) determining barcode sequences in the resultant amplified fragments to identify fragments having the same barcode sequence as fragments derived from the same cell.

7. The method according to claim 6, wherein the capturing step serving as the step (1) comprises the following steps:
(1-1) inoculating cells onto the microplate to arrange the cells in the reaction wells in a manner where one bead and one cell are present as a single unit in each reaction well, followed by covering of the microplate with a semipermeable membrane;
(1-2) extracting nucleic acids from each cell by adding a nucleic acid extraction reagent from above the semipermeable membrane to dissolve each cell in each reaction well; and
(1-3) capturing the nucleic acids extracted from each cell by the single-stranded oligonucleotides on each bead.

8. The method according to claim 7, further comprising, after the step (1-3), collecting the beads arranged in the reaction wells of the microplate and having captured nucleic acids in one container to collect the nucleic acids derived from a plurality of cells in the one container.

9. The method according to claim 6, wherein the nucleic acids derived from the cell comprise mRNAs, the nucleic acid capture sequence in the oligonucleotides on each bead comprises an oligo(dT) sequence, and the step (2) further comprises performing a reverse transcription reaction before the nucleic acid amplification reaction.

10. A method of analyzing a composition of nucleic acids derived from a single cell using the microplate of claim 1, the method comprising the following steps:
(1) preparing a plurality of beads obtained by capturing nucleic acids derived from a single cell by single-stranded oligonucleotides on each bead;
(2) performing a nucleic acid amplification reaction using, as templates, the nucleic acids captured by the single-stranded oligonucleotides on each bead to produce amplified fragments; and
(3) determining barcode sequences in the resultant amplified fragments to identify fragments having the same barcode sequence as fragments derived from the same cell.

11. The method according to claim 10, wherein the beads obtained by capturing nucleic acids by single-stranded oligonucleotides in the step (1) are prepared by the following steps:
(1-1) inoculating cells onto the microplate to arrange the cells in the reaction wells in a manner where one bead and one cell are present as a single unit in each reaction well, followed by covering of the microplate with a semipermeable membrane;

(1-2) extracting nucleic acids from each cell by adding a nucleic acid extraction reagent from above the semipermeable membrane to dissolve each cell in each reaction well; and (1-3) capturing the nucleic acids extracted from each cell by the single-stranded oligonucleotides on each bead.

12. The method according to claim 11, further comprising, after the step (1-3), collecting the beads arranged in the reaction wells of the microplate and having captured nucleic acids in one container to collect the nucleic acids derived from a plurality of cells in the one container.

13. The method according to claim 10, wherein the nucleic acids derived from the cell comprise mRNAs, the nucleic acid capture sequence in the oligonucleotides on each bead comprises an oligo(dT) sequence, and the step (2) further comprises performing a reverse transcription reaction before the nucleic acid amplification reaction.

* * * * *